(12) United States Patent
Shoenfeld et al.

(10) Patent No.: US 9,975,944 B2
(45) Date of Patent: May 22, 2018

(54) SYNTHETIC PEPTIDES FOR THE TREATMENT OF AUTOIMMUNE DISEASES

(71) Applicant: TEL HASHOMER MEDICAL RESEARCH INFRASTRUCTURE AND SERVICES LTD., Ramat Gan (IL)

(72) Inventors: Yehuda Shoenfeld, Ramat Gan (IL); Howard Amital, Gedera (IL); Smadar Gertel, Herzeliya (IL)

(73) Assignee: TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 152 days.

(21) Appl. No.: 14/774,088

(22) PCT Filed: Mar. 11, 2014

(86) PCT No.: PCT/IL2014/050243
§ 371 (c)(1),
(2) Date: Sep. 9, 2015

(87) PCT Pub. No.: WO2014/141244
PCT Pub. Date: Sep. 18, 2014

(65) Prior Publication Data
US 2016/0024183 A1 Jan. 28, 2016

Related U.S. Application Data

(60) Provisional application No. 61/776,801, filed on Mar. 12, 2013.

(51) Int. Cl.
| | |
|---|---|
| *A61K 38/00* | (2006.01) |
| *A61K 39/00* | (2006.01) |
| *C07K 14/78* | (2006.01) |
| *C07K 14/75* | (2006.01) |
| *C07K 14/47* | (2006.01) |
| *C12N 9/88* | (2006.01) |

(52) U.S. Cl.
CPC .............. *C07K 14/78* (2013.01); *A61K 38/00* (2013.01); *C07K 14/47* (2013.01); *C07K 14/4713* (2013.01); *C07K 14/75* (2013.01); *C12N 9/88* (2013.01); *C12Y 402/01011* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,843,456 A | 12/1998 | Paoletti | |
| 5,869,270 A | 2/1999 | Rhode | |
| 5,869,279 A | 2/1999 | Camiener | |
| 8,198,401 B2 | 6/2012 | Hill | |
| 2004/0123343 A1* | 6/2004 | La Rosa | C07K 14/415 800/278 |
| 2009/0298778 A1 | 12/2009 | Clavel | |
| 2010/0216173 A1 | 8/2010 | Haro Villar | |
| 2012/0225820 A1 | 9/2012 | Hill | |

FOREIGN PATENT DOCUMENTS

| | | |
|---|---|---|
| EP | 0949270 | 10/1999 |
| EP | 2161284 | 3/2010 |
| WO | WO1999028344 | * 6/1999 |
| WO | 2004015056 | 2/2004 |
| WO | 2008/090360 | 7/2008 |
| WO | 2010/085763 | 7/2010 |
| WO | 2010117694 | 10/2010 |
| WO | 2013/014312 | 1/2013 |

OTHER PUBLICATIONS

Hueber et al. Antigen microarray profiling of autoantibodies in rheumatoid arthritis. Arthritis Rheum 2005;52:2645-55.*
Levesque et al. Anti-Cyclic Citrullinated Peptide Testing for the Diagnosis of Rheumatoid Arthritis and the Quest for Improved Sensitivity and Predictive Value. Arthritis & Rheumatism vol. 60, No. 8, Aug. 2009, pp. 2211-2215.*
Kidd et al. Epitope spreading to citrullinated antigens in mouse models of autoimmune arthritis and demyelination. Arthritis Research & Therapy 2008, 10:R119.*
Application Notes Antibody signatures defined by high-content peptide microarray analysis. Nature Methods 6, Mar. 2009, p. 1-4.*
Hansson, M., et al. Validation of a multiplex chip-based assay for the detection of autoantibodies against citrullinated peptides. Arthritis Res Ther 14, R201 (2012).*
Kampstra et al. HLA class II and rheumatoid arthritis: the bumpy road of revelation. Immunogenetics (2017) 69:597-603. (Year: 2017).*
Van Noort JM, Amor S. Cell biology of autoimmune diseases. Int Rev Cytol. 178:127-206, 1998. (Year: 1998).*
Amital et al., Administration of a multi-epitope citrullinated peptide for attenuation of immune response and adjuvant arthritis. ACR/ARHP Annual Meeting, Oct. 28, 2013 (retrieved on Jun. 17, 2014).
Catalán et al., (2012) Weak CD4+ T-cell responses to citrullinated vimentin in rheumatoid arthritis patients carrying HLA-DR9 alleles. Rheumatol Int 32(6): 1819-25 (Published online Jul. 2011).
Feitsma et al., (2010) Identification of citrullinated vimentin peptides as T cell epitopes in HLA-DR4-positive patients with rheumatoid arthritis. Arthritis & Rheumatism 62(1): 117-25.

(Continued)

*Primary Examiner* — Maher M Haddad

(74) *Attorney, Agent, or Firm* — Dorsey & Whitney LLP

(57) ABSTRACT

The present invention provides synthetic peptides, including peptides comprising a plurality of epitopes, each epitope being derived from a different protein, and peptides comprising a plurality of citrullinated residues. The present invention also related to use of said peptides for the treatment of autoimmune diseases and disorder.

13 Claims, 20 Drawing Sheets

(56) References Cited

OTHER PUBLICATIONS

Gertel et al., (2015) Immune tolerance induction with multiepitope peptide derived from citrullinated autoantigens attenuates arthritis manifestations in adjuvant arthritis rats. J Immunol 194(12): 5674-80.

Gregersen et al., (1987) The shared epitope hypothesis. An approach to understanding the molecular genetics of susceptibility to rheumatoid arthritis. Arthritis & Rheumatism 30(11): 1205-13.

Harre et al., (2012) Induction of osteoclastogenesis and bone loss by human autoantibodies against citrullinated vimentin. J Clin Invest 122(5): 1791-802.

Hugues et al., (2002) Generation and use of alternative multimers of peptide/MHC complexes. J Immunol Methods 268 (1): 83-92.

Kaushansky et al., (2011) 'Multi-epitope-targeted' immune-specific therapy for a multiple sclerosis-like disease via engineered multi-epitope protein is superior to peptides. PLoS One 6(11): e27860.

Kuhn et al., (2006) Antibodies against citrullinated proteins enhance tissue injury in experimental autoimmune arthritis. J Clin Invest 116(4): 961-73.

Meyer et al., (2003) Anticitrullinated protein/peptide antibody assays in early rheumatoid arthritis for predicting five year radiographic damage. Ann Rheum Dis 62(2): 120-6.

Shin et al., (2013) Role of citrullinated fibrinogen peptides in the activation of CD4 T cells from patients with rheumatoid arthritis. Immune Network 13(4): 116-22.

Thomas et al., (2011) Safety and preliminary evidence of efficacy in a phase I clinical trial of autologous tolerising dendritic cells exposed to citrullinated peptides (Rheumavax) in patients with rheumatoid arthritis. Ann Rheum Dis 70 (Suppl3): 169.

von Delwig et al., (2010) Response of Th17 cells to a citrullinated arthritogenic aggrecan peptide in patients with rheumatoid arthritis. Arthritis & Rheumatism 62(1): 143-9.

Malakoutikhah et al., (2011) the use of chimeric vimentin citrullinated peptides for the diagnosis of rheumatoid arthritis. Med Chem 54(21): 7486-92.

Aggarwal et al., (2013) T cell responses to citrullinated self-peptides in patients with rheumatoid arthritis. Rheumatol Int (9): 2359-63.

Aletaha et al., (2010) 2010 Rheumatoid arthritis classification criteria: an American College of Rheumatology/European League Against Rheumatism collaborative initiative. Arthritis Rheum 62(9): 2569-81.

Arnson et al., (2010) Effects of tobacco smoke on immunity, inflammation and autoimmunity. J Autoimmun 34(3): U258-65.

Auger et al., (2005) Influence of HLA-DR genes on the production of rheumatoid arthritis-specific autoantibodies to citrullinated fibrinogen. Arthritis Rheum 52(11): 3424-32.

Clavel et al., (2008) Induction of macrophage secretion of tumor necrosis factor alpha through Fcgamma receptor IIa engagement by rheumatoid arthritis-specific autoantibodies to citrullinated proteins complexed with fibrinogen. Arthritis Rheum 58(3): 678-88.

Gertel et al., (2017) Immunomodulation of RA Patients' PBMC with a Multiepitope Peptide Derived from Citrullinated Autoantigens. Mediators Inflamm 2017: 3916519; 9 pages.

Goules et al., (2013) Fine specificity of anti-citrullinated peptide antibodies discloses a heterogeneous antibody population in rheumatoid arthritis. Clin Exp Immunol 174(1): 10-7.

Hamilton (2008) Colony-stimulating factors in inflammation and autoimmunity. Nat Rev Immunol 8(7): 533-44.

Iobagiu et al., (2011) The antigen specificity of the rheumatoid arthritis-associated ACPA directed to citrullinated fibrin is very closely restricted. J Autoimmun 37(4): 263-72.

Khandpur et al., (2013) NETs are a source of citrullinated autoantigens and stimulate inflammatory responses in rheumatoid arthritis. Sci Transl Med 5(178): 178ra40; 11 pages.

Laurent et al., (2011) Fcγ receptor profile of monocytes and macrophages from rheumatoid arthritis patients and their response to immune complexes formed with autoantibodies to citrullinated proteins. Ann Rheum Dis 70(6): 1052-9.

Lu et al., (2010) Anti-citrullinated protein antibodies bind surface-expressed citrullinated Grp78 on monocyte/macrophages and stimulate tumor necrosis factor alpha production. Arthritis Rheum 62(5): 1213-23.

Lundberg et al., (2005) Citrullinated proteins have increased immunogenicity and arthritogenicity and their presence in arthritic joints correlates with disease severity. Arthritis Res Ther 7(3): R458-67.

Nishimura et al., (2007) Meta-analysis: diagnostic accuracy of anti-cyclic citrullinated peptide antibody and rheumatoid factor for rheumatoid arthritis. Ann Intern Med 146(11): 797-808.

Snir et al., (2010) Antibodies to several citrullinated antigens are enriched in the joints of rheumatoid arthritis patients. Arthritis Rheum 62(1): 44-52.

Syversen et al., (2008) High anti-cyclic citrullinated peptide levels and an algorithm of four variables predict radiographic progression in patients with rheumatoid arthritis: results from a 10-year longitudinal study. Ann Rheum Dis 67(2): 212-7.

van Venrooij et al., (2011) Anti-CCP antibodies: the past, the present and the future. Nat Rev Rheumatol 7(7): 391-8.

Yoshida et al., (2014) Citrullination of epithelial neutrophil-activating peptide 78/CXCL5 results in conversion from a non-monocyte-recruiting chemokine to a monocyte-recruiting chemokine. Arthritis Rheumatol 66(10): 2716-27.

\* cited by examiner

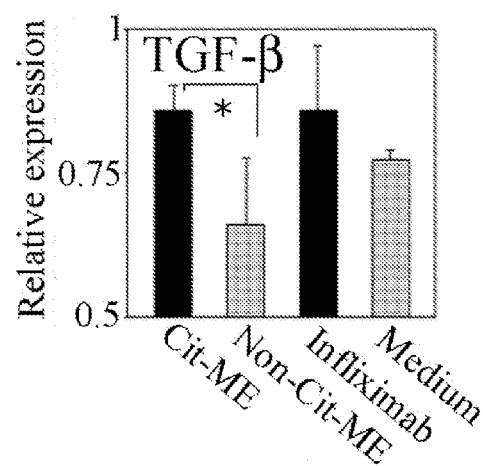
FIGURE 5A
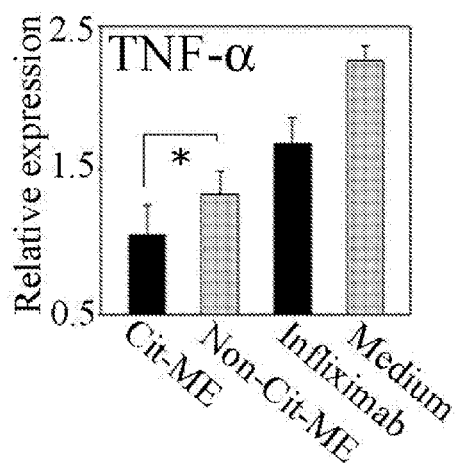 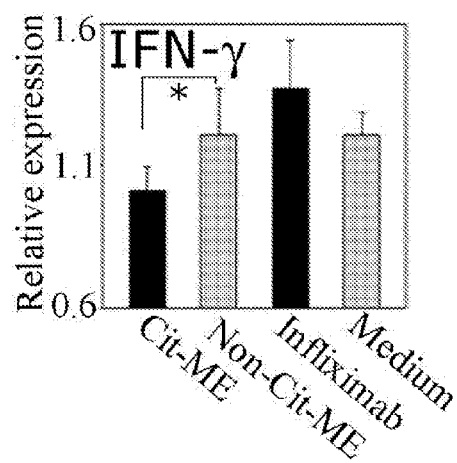
FIGURE 5B	FIGURE 5C

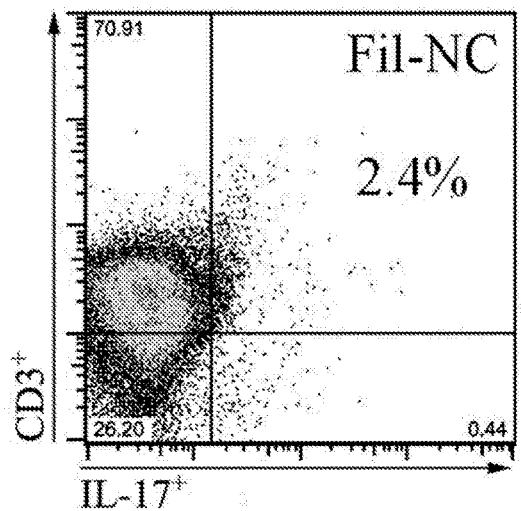
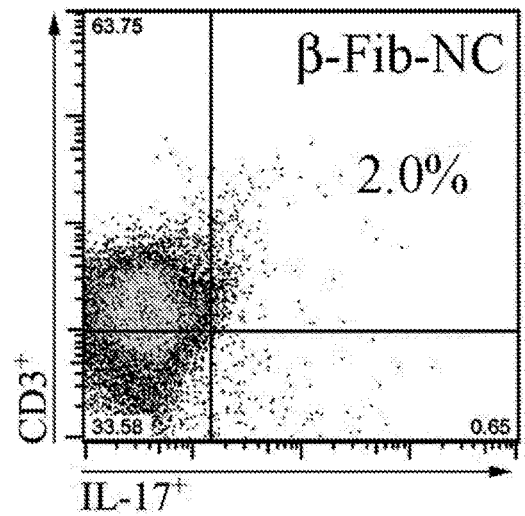
FIGURE 7A   FIGURE 7B
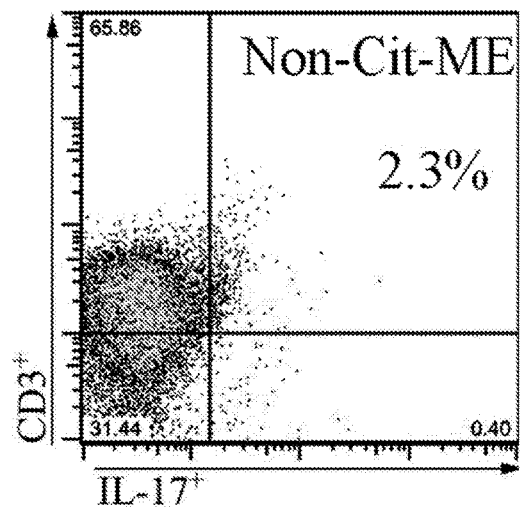
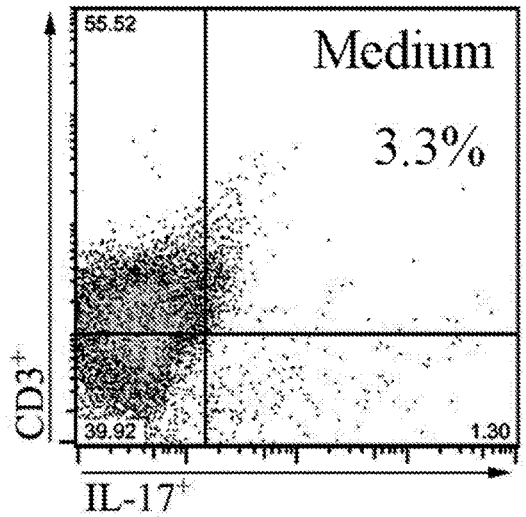
FIGURE 7C   FIGURE 7D

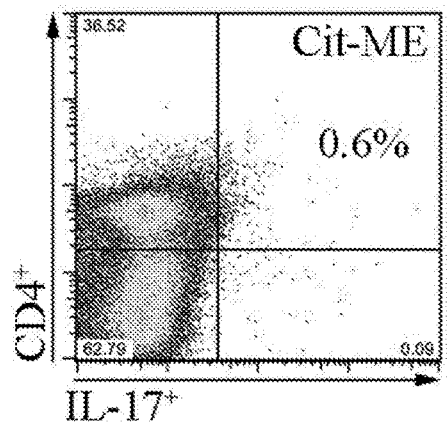
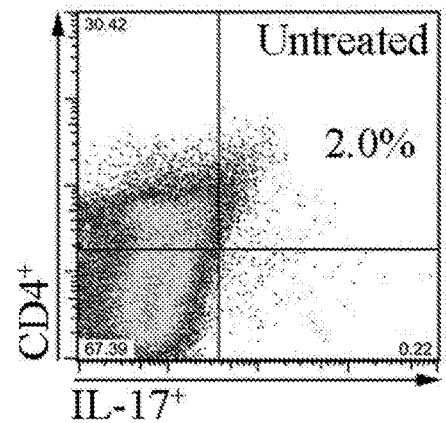
FIGURE 13A  FIGURE 13B
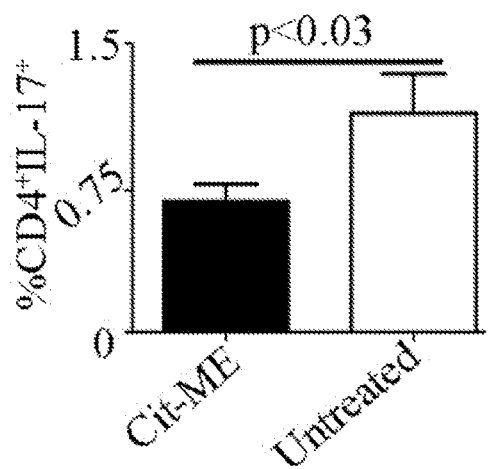
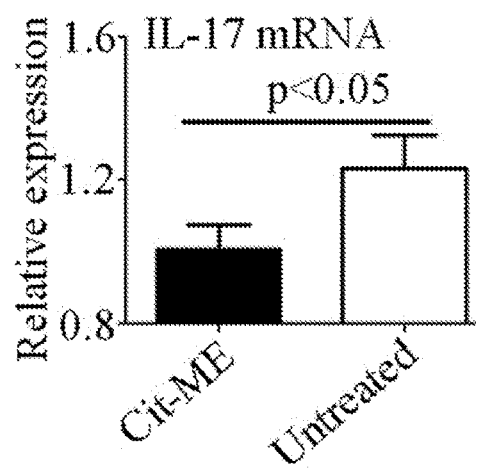
FIGURE 13C  FIGURE 13D

US 9,975,944 B2

SYNTHETIC PEPTIDES FOR THE TREATMENT OF AUTOIMMUNE DISEASES

CROSS-REFERENCE TO RELATED APPLICATIONS

This application is a national stage application of International Application No. PCT/IL2014/050243, filed Mar. 11, 2014, and entitled "SYNTHETIC PEPTIDES FOR THE TREATMENT OF AUTOIMMUNE DISEASES", which claims priority to U.S. Application No. 61/776,801, filed Mar. 12, 2013, and entitled "CITRULLINATED PEPTIDES FOR THE TREATMENT OF RHEUMATOID ARTHRITIS", both of which are hereby incorporated by reference herein in their entireties for all purposes.

FIELD OF THE INVENTION

The present invention relates to synthetic peptides, including peptides comprising a plurality of epitopes, each epitope being derived from a different protein, and peptides comprising a plurality of citrullinated residues. The present invention also relates to use of said peptides for the treatment of autoimmune diseases and disorders.

BACKGROUND OF THE INVENTION

The immune response in autoimmune conditions, such as, rheumatoid arthritis (RA), is dominated by the production of autoantibodies against 'self'-antigens. Many of those rheumatoid arthritis-specific autoantibodies are generated against citrullinated antigens, such as, citrulline residues on, for example, fibrin, filaggrin and vimentin.

Citrullination is the post-translational conversion of arginine to citrulline by the enzyme peptidylarginine deiminase that is up-regulated under inflammatory conditions. This process evokes an autoreactivity towards the citrullinated residues, leading to the development of rheumatoid arthritis in susceptible individuals, among other factors.

Citrullinated peptides are typically used as a biomarker diagnostic tool in rheumatoid arthritis patients for serologic detection of anti-citrullinated protein antibodies. However, anti-citrullinated protein antibodies can be detected even before the onset of the disease symptoms and are associated with a more aggressive disease course (Meyer O. et al. Ann Rheum Dis 2003; 62:120-6).

US 2012/0225820 to Hill et al. disclose citrullinated antigenic peptides associated with rheumatoid arthritis.

Delwig et al. (Arthrithis & Rheumatism, 62(1): 143-149, 2010) disclose the proliferative response of peripheral blood mononuclear cells (PBMCs) to citrullinated aggrecan peptide in RA patients and not in healthy controls. Delwig et at further disclose the lack of response to noncitrullinated analog peptide and suggests the use of citrullinated aggrecan peptide as a biomarker to RA.

Feitsma et al. (Arthrithis & Rheumatism, 62(1): 117-125, 2010) disclose citrullinated vimentin peptides naturally processed and recognized by peptide-specific T cells of RA patients.

Catalan et al. (Reumatol Int., 32: 1819-1825, 2012) disclose CD4+ T-cells response to citrullinated vimentin in RA patients.

Shin et al. (Immune Network, 13(4):116-122, 2013) discloses CD4+ T-cells response to citrullinated fibrinogen in RA patients.

There remains an unmet need for therapeutic approaches for the treatment of autoimmune diseases, such as, rheumatoid arthritis which do not involve broad immune suppression.

SUMMARY OF THE INVENTION

The present invention discloses novel peptides as well as the use of said peptides as tolerogenic agents for restoration of immune-tolerance while avoiding general immune suppression. As such, the present invention encompasses the use of the peptides of the invention in the treatment of autoimmune diseases and disorders, such as, rheumatoid arthritis.

Unexpectedly, the peptides of the invention induce significant up regulation in the expression of TGF-β, an anti-inflammatory gene, and a significant down regulation in the expression of pro-inflammatory genes, IFN-γ, TNF-α and IL-17, in PBMCs obtained from RA patients. Surprisingly, in the presence of the peptides of the invention arthritis signs (e.g. mean paw diameter and arthritis score) are reduced in a rat model for RA.

There is provided, in accordance with an embodiment, a synthetic peptide, said synthetic peptide comprising a plurality of epitopes, each epitope being derived from a protein selected from the group consisting of: vimentin, filaggrin, beta-fibrinogen, collagen, α-enolase, fibrinogen-a, aggrecan and any combination thereof, wherein at least one epitope comprises at least one citrullinated residue. Each possibility is a separate embodiment of the invention.

In some embodiments, the synthetic peptide comprises a plurality of epitopes, each epitope being derived from a protein selected from the group consisting of: vimentin, filaggrin, beta-fibrinogen, collagen, α-enolase, fibrinogen-a, aggrecan and any combination thereof, wherein at least one epitope comprises at least one arginine or at least one citrullinated residue. Each possibility is a separate embodiment of the invention.

In some embodiments, each epitope of said plurality of epitopes is derived from a different protein.

In some embodiment, each epitope comprises a sequence of 5 to 15 amino acids.

In some embodiments, the synthetic peptide comprises 10 to 60 amino acid residues.

In some embodiments, said synthetic peptide comprises at least three epitopes. In some embodiments, said synthetic peptide comprises at least four epitopes. In some embodiments, said synthetic peptide consists of four epitopes.

In some embodiments, said synthetic peptide comprises a plurality of epitopes wherein at least one epitope comprises at least one arginine. In some embodiments, said synthetic peptide comprises a plurality of epitopes wherein each epitope comprises at least one arginine. In other embodiments, said synthetic peptide comprises a plurality of epitopes wherein at least one epitope comprises a plurality of arginine residues.

In some embodiments, said synthetic peptide comprises a plurality of epitopes, wherein at least one epitope comprises at least one citrullinated residue. In some embodiments, said synthetic peptide comprises at least one epitope, wherein said epitope comprises a plurality of citrullinated residues.

In some embodiments, said synthetic peptide comprises at least two citrullinated residues. In other embodiments, said synthetic peptide comprises at least three citrullinated residues. In yet other embodiments, said synthetic peptide comprises five citrullinated residues.

In some embodiments, said synthetic peptide comprises at least one epitope derived from beta-fibrinogen; at least one epitope derived from fillagrin; at least one epitope derived from vimentin; and at least one epitope derived from collagen.

In some embodiments, said synthetic peptide comprises a plurality of epitopes selected from the group consisting of: VRLRSSV (SEQ ID NO: 5); ESTRGRS (SEQ ID NO: 6); RPAPPP (SEQ ID NO: 7); ARGLT (SEQ ID NO: 8); VCitLRSSV (SEQ ID NO: 9); VRLCitSSV (SEQ ID NO: 10); VCitLCitSSV (SEQ ID NO: 11); ESTCitGRS (SEQ ID NO: 12); ESTRGCitS (SEQ ID NO: 13); ESTCitGCitS (SEQ ID NO: 14); CitPAPPP (SEQ ID NO: 15) and ACit-GLT (SEQ ID NO: 16). Each possibility is a separate embodiment of the invention.

In some embodiments, said plurality of epitopes are selected from the group consisting of: VRLRSSV (SEQ ID NO: 5); ESTRGRS (SEQ ID NO: 6); RPAPPP (SEQ ID NO: 7); and ARGLT (SEQ ID NO: 8). Each possibility is a separate embodiment of the invention.

In other embodiments, said plurality of epitopes are selected from the group consisting of: VCitLRSSV (SEQ ID NO: 9); VRLCitSSV (SEQ ID NO: 10); VCitLCitSSV (SEQ ID NO: 11); ESTCitGRS (SEQ ID NO: 12); ESTRGCitS (SEQ ID NO: 13); ESTCitGCitS (SEQ ID NO: 14); CitPAPPP (SEQ ID NO: 15) and ACitGLT (SEQ ID NO: 16).

In some embodiments, said synthetic peptide comprises the amino acid sequence VCitLCitSSVESTCitGRSCitPAP-PPACitGLT (SEQ ID NO: 1), or an analog or derivative thereof.

In some embodiments, the synthetic citrullinated peptide consists of the sequence set forth in SEQ ID NO: 1, or an analog or derivative thereof.

In some embodiments, the peptide has an amino acid sequence that differs from SEQ ID NO: 1 by one or more conservative amino acid substitutions. Additionally or alternatively, the peptide has an amino acid sequence that differs from SEQ ID NO: 1 by one or more single mutations, wherein each single mutation represents a single amino acid deletion, insertion or substitution. Each possibility is a separate embodiment of the invention.

In some embodiments, said synthetic peptide comprises the amino acid sequence VRLRSSVESTRGRSRPAPPPAR-GLT (SEQ ID NO: 4), or an analog or derivative thereof. In some embodiments, said synthetic peptide consists of the amino acid sequence set forth in SEQ ID NO: 4.

In some embodiments, said peptide has an amino acid sequence that differs from SEQ ID NO: 4 by one or more conservative amino acid substitutions. In some embodiments, said peptide has an amino acid sequence that differs from SEQ ID NO: 4 by one or more single mutations, wherein each single mutation represents a single amino acid deletion, insertion or substitution.

There is provided, in accordance with an embodiment, a synthetic citrullinated peptide comprising at least two citrullinated residues, wherein said peptide is derived from a protein selected from the group consisting of: vimentin, filaggrin, beta-fibrinogen, collagen, α-enolase, fibrinogen-a and aggrecan. Each possibility represents a separate embodiment.

In some embodiments, said synthetic citrullinated peptide comprises at least three citrullinated residues. In some embodiments, said synthetic citrullinated peptide comprises at least four citrullinated residues. In other embodiments, said synthetic citrullinated peptide comprises at least five citrullinated residues.

In some embodiments, said synthetic citrullinated peptide is derived from beta-fibrinogen. In some embodiments, said synthetic citrullinated peptide comprises the amino acid sequence CitPAPPPISGGGYCitACit (SEQ ID NO: 2). In some embodiments, said synthetic citrullinated peptide is consisting of the amino acid sequence set forth in SEQ ID NO: 2.

In some embodiments, said peptide has an amino acid sequence that differs from SEQ ID NO: 2 by one or more conservative amino acid substitutions. In some embodiments, said peptide has an amino acid sequence that differs from SEQ ID NO: 2 by one or more single mutations, wherein each single mutation represents a single amino acid deletion, insertion or substitution.

In some embodiments, said synthetic citrullinated peptide is derived from collagen. In some embodiments, said synthetic citrullinated peptide is derived from collagen type II. In some embodiments, said synthetic citrullinated peptide comprises the amino acid sequence ACitGLTGCitPGDAK (SEQ ID NO: 21). In some embodiments, said synthetic citrullinated peptide is consisting of the amino acid sequence set forth in SEQ ID NO: 21.

In some embodiments, said peptide has an amino acid sequence that differs from SEQ ID NO: 21 by one or more conservative amino acid substitutions. In some embodiments, said peptide has an amino acid sequence that differs from SEQ ID NO: 21 by one or more single mutations, wherein each single mutation represents a single amino acid deletion, insertion or substitution. Each possibility is a separate embodiment of the invention.

There is provided, in accordance with an embodiment, a pharmaceutical composition comprising as an active ingredient a synthetic peptide and a pharmaceutically acceptable carrier, wherein said peptide comprises a plurality of epitopes, each epitope being derived from a different protein and wherein at least one epitope comprises at least one arginine or at least one citrullinated residue. Each possibility is a separate embodiment of the invention.

In some embodiments, each protein is selected from the group consisting of: vimentin, filaggrin, beta-fibrinogen, collagen, α-enolase, fibrinogen-a, aggrecan and any combination thereof. Each possibility is a separate embodiment of the invention.

In some embodiments, said pharmaceutical composition comprises a synthetic peptide comprising at least three epitopes. In some embodiments, said pharmaceutical composition comprises a synthetic peptide comprising at least four epitopes. In some embodiments, said pharmaceutical composition comprises a synthetic peptide consisting of four epitopes.

In some embodiments, said synthetic peptide comprises a plurality of epitopes selected from the group consisting of: VRLRSSV (SEQ ID NO: 5); ESTRGRS (SEQ ID NO: 6); RPAPPP (SEQ ID NO: 7); ARGLT (SEQ ID NO: 8); VCitLRSSV (SEQ ID NO: 9); VRLCitSSV (SEQ ID NO: 10); VCitLCitSSV (SEQ ID NO: 11); ESTCitGRS (SEQ ID NO: 12); ESTRGCitS (SEQ ID NO: 13); ESTCitGCitS (SEQ ID NO: 14); CitPAPPP (SEQ ID NO: 15) and ACit-GLT (SEQ ID NO: 16). Each possibility is a separate embodiment of the invention.

There is provided, in accordance with an embodiment, a pharmaceutical composition comprising as an active ingredient a synthetic citrullinated peptide and a pharmaceutically acceptable carrier, wherein said peptide comprises at least two citrullinated residues, and wherein said peptide is derived from a protein selected from the group consisting of: vimentin, filaggrin, beta-fibrinogen, collagen, α-enolase, fibrinogen-a and aggrecan. Each possibility is a separate embodiment of the invention.

In some embodiments, said pharmaceutical composition comprises a synthetic peptide comprising at least three citrullinated residues.

In some embodiments, said pharmaceutical composition comprises a synthetic citrullinated peptide comprising the amino acid sequence CitPAPPPISGGGYCitACit (SEQ ID NO: 2).

In some embodiments, said pharmaceutical composition comprises a synthetic citrullinated peptide comprising the amino acid sequence ACitGLTGCitPGDAK (SEQ ID NO: 21).

There is provided, in accordance with an embodiment, a pharmaceutical composition comprising a synthetic peptide and a pharmaceutically acceptable carrier for use in the treatment of an autoimmune disease or disorder, wherein said peptide comprises a plurality of epitopes, each epitope being derived from a different protein and wherein at least one epitope comprises at least one arginine or at least one citrullinated residue. In some embodiments, each protein is selected from the group consisting of: vimentin, filaggrin, beta-fibrinogen, collagen, α-enolase, fibrinogen-a, aggrecan and any combination thereof. Each possibility is a separate embodiment of the invention.

In some embodiments, said pharmaceutical composition is used for treating autoimmune disease, wherein treating comprises reducing the symptoms associated with said autoimmune disease or disorder, reducing the severity of said autoimmune disease or disorder, ameliorating said autoimmune disease or disorder, inhibiting further progression of said autoimmune disease or disorder, curing said autoimmune disease or disorder and any combination thereof.

In some embodiments, said synthetic peptide comprises a plurality of epitopes selected from the group consisting of: VRLRSSV (SEQ ID NO: 5); ESTRGRS (SEQ ID NO: 6); RPAPPP (SEQ ID NO: 7); ARGLT (SEQ ID NO: 8); VCitLRSSV (SEQ ID NO: 9); VRLCitSSV (SEQ ID NO: 10); VCitLCitSSV (SEQ ID NO: 11); ESTCitGRS (SEQ ID NO: 12); ESTRGCitS (SEQ ID NO: 13); ESTCitGCitS (SEQ ID NO: 14); CitPAPPP (SEQ ID NO: 15) and ACitGLT (SEQ ID NO: 16). Each possibility is a separate embodiment of the invention.

There is provided, in accordance with an embodiment, a pharmaceutical composition comprising a synthetic citrullinated peptide and a pharmaceutically acceptable carrier for use in the treatment of an autoimmune disease or disorder, wherein said synthetic citrullinated peptide comprises at least two citrullinated residues, and wherein said peptide is derived from a protein selected from the group consisting of: vimentin, filaggrin, beta-fibrinogen, collagen, α-enolase, fibrinogen-a and aggrecan.

In some embodiments, said pharmaceutical composition comprises a synthetic citrullinated peptide comprising the amino acid sequence CitPAPPPISGGGYCitACit (SEQ ID NO: 2).

In some embodiments, said pharmaceutical composition comprises a synthetic citrullinated peptide comprising the amino acid sequence ACitGLTGCitPGDAK (SEQ ID NO: 21).

In some embodiments, the treatments are as described hereinabove.

There is provided, in accordance with an embodiment, a method of treating an autoimmune disease comprising administering to a subject in need thereof a therapeutically effective amount of a pharmaceutical composition comprising a synthetic peptide and a pharmaceutically acceptable carrier, wherein said peptide comprises a plurality of epitopes, each epitope being derived from a different protein and wherein at least one epitope comprises arginine or a citrullinated residue. In some embodiments, the protein is selected from the group consisting of: vimentin, filaggrin, beta-fibrinogen, collagen, α-enolase, fibrinogen-a, aggrecan and any combination thereof. Each possibility is a separate embodiment of the invention.

In some embodiments, the disease is rheumatoid arthritis.

In some embodiments, said synthetic peptide comprises a plurality of epitopes selected from the group consisting of: VRLRSSV (SEQ ID NO: 5); ESTRGRS (SEQ ID NO: 6); RPAPPP (SEQ ID NO: 7); ARGLT (SEQ ID NO: 8); VCitLRSSV (SEQ ID NO: 9); VRLCitSSV (SEQ ID NO: 10); VCitLCitSSV (SEQ ID NO: 11); ESTCitGRS (SEQ ID NO: 12); ESTRGCitS (SEQ ID NO: 13); ESTCitGCitS (SEQ ID NO: 14); CitPAPPP (SEQ ID NO: 15) and ACitGLT (SEQ ID NO: 16). Each possibility is a separate embodiment of the invention.

In some embodiments, said synthetic peptide comprises the amino acid sequence set forth in SEQ ID NO: 1. In other embodiments, said synthetic peptide comprises the amino acid sequence set forth in SEQ ID NO: 4.

In some embodiments, the treatments are as described hereinabove.

In some embodiments said subject is selected from the group consisting of: a subject afflicted with said disease or disorder, a subject afflicted with said disease or disorder wherein said subject is in remission, a subject afflicted with said disease or disorder having manifested symptoms associated with said disease or disorder, and any combination thereof.

In some embodiments, the pharmaceutical composition is administered via a route of administration selected from group consisting of: subcutaneous, topical, transdermal, oral, buccal, sublingual, sublabial, intradermal and any combination thereof. Each possibility is a separate embodiment of the invention.

There is provided, in accordance with an embodiment, a method of treating an autoimmune disease comprising administering to a subject in need thereof a therapeutically effective amount of a pharmaceutical composition comprising a synthetic citrullinated peptide and a pharmaceutically acceptable carrier, wherein said synthetic citrullinated peptide comprises at least two citrullinated residues, and wherein said peptide is derived from a protein selected from the group consisting of: vimentin, filaggrin, beta-fibrinogen, collagen, α-enolase, fibrinogen-a and aggrecan.

There is provided, in accordance with an embodiment, a kit for the treatment of an autoimmune disease or disorder comprising a therapeutically effective amount of a pharmaceutical composition comprising a synthetic citrullinated peptide and a pharmaceutically acceptable carrier, wherein said synthetic citrullinated peptide comprises at least two citrullinated residues, and wherein said peptide is derived from a protein selected from the group consisting of: vimentin, filaggrin, beta-fibrinogen, collagen, α-enolase, fibrinogen-a and aggrecan.

There is provided, in accordance with an embodiment, a kit for the treatment of an autoimmune disease comprising a therapeutically effective amount of a pharmaceutical composition comprising a synthetic peptide and a pharmaceutically acceptable carrier, wherein said peptide comprises a plurality of epitopes, each epitope being derived from a protein selected from the group consisting of: vimentin, filaggrin, beta-fibrinogen, collagen, α-enolase, fibrinogen-a, aggrecan and any combination thereof, and wherein at least one epitope comprises at least one arginine or at least one citrullinated residue.

In some embodiment, the kit further comprises instructions manual, listing the use of each component of the kit and the sequence of use.

The peptides, the disease, the treatments, the subject in need, the kits and means of administering are as described hereinabove.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Exemplary embodiments are illustrated in referenced figures. It is intended that the embodiments and figures disclosed herein are to be considered illustrative rather than restrictive. The figures are listed below.

FIG. 5 shows the effect of Cit-ME, Non-Cit-Me, Infliximab and medium (control) on expression of TGF-β (A), TNF-α (B), and INF-γ (C) in peripheral blood mononuclear cells derived from rheumatoid arthritis patients (*p<0.05).

FIGS. 13A-13C present FACS two dimensional dot plots of CD4$^+$IL-17$^+$ T cells obtained from AIA rats treated with Cit-ME (A) or untreated (B) and the corresponding statistical analysis (C; n=8).

FIG. 13D shows the effect of Cit-ME on IL-17 mRNA expression in the spleen of AIA rats, in comparison to control (untreated) AIA rats (p<0.05).

DETAILED DESCRIPTION OF THE INVENTION

Figure 1A:
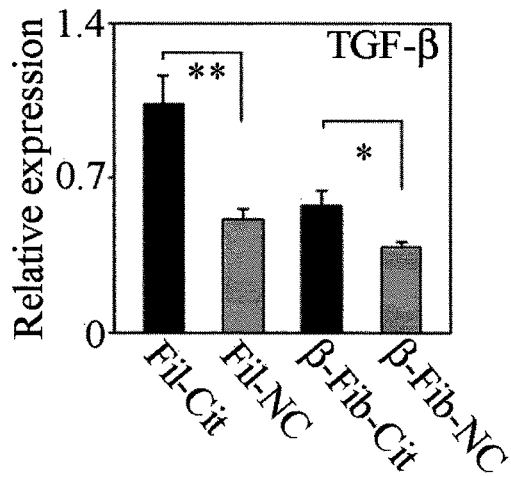
FIG. 1 shows the effect of Fil-Cit, β-Fib-Cit, and their matched non-citrullinated (NC) peptides (Fil-NC and β-Fib-NC, respectively) on gene expression of TGF-β (A), INF-γ (B) TNF-α (C) and IL-17 (D) in peripheral blood mononuclear cells derived from rheumatoid arthritis patients (*p≤0.05, **p≤0.007).

The present invention provides synthetic peptides comprising a plurality of epitopes, each epitope being derived from a different protein, and synthetic peptides comprising a plurality of citrullinated residues, which peptides provide a therapeutic modality for the treatment of autoimmune diseases and disorder. The peptides of the invention may be used as tolerogenic agents for restoration of immune-tolerance without introducing a general immune suppression. As such, the present invention encompasses the use of the peptides of the invention in a therapeutic approach for the treatment of autoimmune diseases and disorder, exemplified herein on RA.

The present invention provides, in some embodiments, a synthetic peptide comprising a plurality of epitopes, each epitope being derived from a different protein.

In some embodiments, the present invention provides, a synthetic peptide comprising a plurality of epitopes, each epitope being derived from a protein selected from the group consisting of: vimentin, filaggrin, beta-fibrinogen, collagen, α-enolase, fibrinogen-a, aggrecan and any combination thereof, wherein at least one epitope comprises arginine or a citrullinated residue.

The protein vimentin typically refers to a protein designated by NCBI accession no.: NP_003371.2.

The protein filaggrin typically refers to a protein designated by NCBI accession no. NP_002007.1.

The protein beta-fibrinogen typically refers to a protein designated by NCBI accession nos.: AAA98115.1; AAA52429.1; NP_005132.2 and NP_001171670.1.

The protein collagen typically refers to a protein designated by NCBI accession nos.: CAA34683.1; AAC41772.1; EAW57967.1; EAW57966.1; EAW57969.1; NP_001835.3; NP_149162.2; NP_001849.2 and NP_000080.2.

The protein α-enolase typically refers to a protein designated by NCBI accession nos.: CAA34360.1; AAB88178.1; NP_001419.1; CAA59331.1 and AAA52387.1.

The protein fibrinogen-a typically refers to a protein designated by NCBI accession nos.: AAB26584.1 and AAB47117.1.

The protein aggrecan typically refers to a protein designated by NCBI accession no.: AAH36445.1.

In some embodiments, the present invention provides a synthetic peptide comprising an amino acid sequence selected from SEQ ID NO: 1 to SEQ ID NO:16, SEQ ID NO:21 and SEQ ID NO:22 and combinations thereof. Each possibility is a separate embodiment of the invention.

Additionally or alternatively, there is provided, in some embodiments, a pharmaceutical composition comprising the synthetic peptide of the invention.

In some embodiments, the pharmaceutical composition comprises a synthetic peptide for the treatment of rheumatoid arthritis, wherein the synthetic peptide comprises
(a) at least two citrullinated residues; or
(b) a plurality of epitopes, each epitope being derived from a different protein, wherein at least one epitope comprises at least one arginine or at least one citrullinated residue; or
(c) a combination of (a) and (b).

In some embodiments, said synthetic peptide comprises at least three citrullinated residues. In some embodiments, said synthetic peptide comprises four citrullinated residues. In some embodiments, said synthetic citrullinated peptide comprises five citrullinated residues.

As used herein, the terms "peptide", "polypeptide" and "protein" interchangeably refer to a chain of amino acid residues.

The peptide epitope, as used herein, refers to a chain of 5 to 15 amino acid residues on average.

As used herein and in the claims the term "plurality" means at least two. The peptides comprising a plurality of epitopes typically comprise 10-60 amino acids.

In some embodiments, the peptide is a chain of 6 to 25 amino acid residues.

In some embodiments, the peptide is a chain of amino acids that are derived from the known human amino acid sequence of the relevant proteins.

In some embodiments, the epitopes encompassed within the peptides of the invention are arthritic related autoantigen epitopes. As used herein and further detailed below, an "arthritic related autoantigen epitope" or a "rheumatoid arthritis related autoantigen epitope" or an "epitope" refer to an epitope having a sequence of 3 to 15 amino acids, that is a target of the rheumatoid arthritis autoantibodies, including, anti-citrullinated peptide antibodies. This epitope can be presented by antigen-gene presenting cells to other immune cells to induce tolerance. Rheumatoid arthritis related autoantigen epitope include, but is not limited to, an epitope derived from a rheumatoid arthritis related proteins. Rheumatoid arthritis related proteins include, but are not limited to, beta-fibrinogen, collagen, filaggrin, vimentin, α-enolase, fibrinogen-a and aggrecan. As such, the invention encompasses peptides that can be presented by antigen presenting cells to other immune cells to induce tolerance.

Anti-citrullinated peptide antibodies are found in rheumatoid arthritis patients with HLA-DRB1 alleles. The products of these alleles share a 5AA sequence in a peptide-binding pocket termed the shared epitope (SE). The citrullinated self-peptides bound to the antigen pocket of the SE alleles are presented to T cells and lead to a chronic autoimmune response against citrullinated peptides and to rheumatoid arthritis. It is understood by the skilled in the art that an arthritic related citrullinated autoantigen epitope has the property of binding MHC Class II molecules with a shared epitope (SE), Furthermore, it is understood by the skilled in the art that binding of an arthritic related citrullinated autoantigen epitope to a MHC Class II molecules with a shared epitope give rise to activated T cells.

As used herein and further detailed below, the term "arthritic related citrullinated autoantigen epitope" also refers to an epitope that may be presented by antigen-gene presenting cells to other immune cells to induce tolerance.

As used herein the terms "citrullinated peptide" refers to a peptide having at least one citrullinated residue. In some embodiments, the citrullinated peptide refers to a peptide having at least two, or at least three citrullinated residues. In some embodiments, a citrullinated peptide may comprise at least one arginine residue adapted to be citrullinated upon administration. It is understood by the skilled in the art that the additional arginine residues citrullinated upon administration may be citrullinated in vivo by the enzyme peptidylarginine deiminase by deiminating arginine into citrulline.

The terms "citrullinated residue" and "citrulline" as used herein are interchangeable.

In further embodiments, the peptides of the invention also encompass peptides that have been modified by, for example, phosphorylation, glycosylation or lipidation. Furthermore, the peptides of the present invention may also encompass "functionally equivalent variants" or "analogues" of the peptides. As such, this would include, but not be limited to, peptides and polypeptides with partial sequence homology, peptides having one or more specific conservative and/or non-conservative amino acid changes and peptide conjugates which do not alter the biological or structural properties of the peptide.

In some embodiments the peptide may be derived from, for example, vimentin, fibrinogen filaggrin, collagen α-enolase, fibrinogen-a, aggrecan or combinations thereof. Each possibility is a separate embodiment of the invention.

As a non-limiting example, the synthetic peptide may have an amino acid sequence comprising a plurality of arthritic related autoantigen epitopes. Alternatively, the amino acid sequence comprises at least three arthritic related autoantigen epitopes. Additionally or alternatively, the synthetic peptide may have an amino acid sequence comprising at least three arthritic related autoantigen epitopes. In exemplary embodiments, the synthetic peptide having an amino acid sequence comprising four arthritic related autoantigen epitopes. In exemplary embodiments, the peptide comprises arginine residues that may be citrullinated by the enzyme peptidylarginine deiminase in vivo by deiminating arginine into citrulline. In some embodiments, the peptides are synthesized and provided as citrullinated ex vivo (in vitro). In other embodiments, the autoantigen epitopes comprise arginine residues that may be enzymatically citrullinated in vivo.

In some embodiments, the synthetic peptide is a multi-epitope peptide, comprising a plurality of epitopes, wherein each epitope of said plurality of epitopes being derived from a different protein. In some embodiments, the synthetic peptide comprises at least three epitopes. In some embodiments, at least one epitope of said plurality of epitopes comprises at least one arginine. In some embodiments, each epitope of said plurality of epitopes comprises at least one arginine. In some embodiments, at least one epitope of said plurality of epitopes comprises a plurality of arginine residues. In some embodiments the synthetic peptide comprises at least two arginine residues.

The term "multiepitope peptide" refers to a chimeric peptide which is made of a plurality of epitopes, where each epitope in said plurality of epitopes is derived from a different, distinct protein.

In some embodiments the synthetic peptide comprises a plurality of epitopes, wherein at least one epitope of said plurality of epitopes comprises at least one citrullinated residue. In some embodiments each epitope of said plurality of epitopes comprises at least one citrullinated residue. In some embodiments at least one epitope of said plurality of epitopes comprises a plurality of citrullinated residues. In some embodiments the synthetic peptide comprises at least two citrullinated residues. In some embodiments the synthetic peptide comprises at least three citrullinated residues.

In some embodiments said synthetic peptide comprises at least one epitope derived from beta-fibrinogen; at least one epitope derived from fillagrin; at least one epitope derived from vimentin; and at least one epitope derived from collagen. Each possibility is a separate embodiment of the invention.

In some embodiments the synthetic peptide comprises a plurality of arthritic related autoantigen epitopes selected from the group consisting of: VRLRSSV (SEQ ID NO: 5); ESTRGRS (SEQ ID NO: 6); RPAPPP (SEQ ID NO: 7); ARGLT (SEQ ID NO: 8); VCitLRSSV (SEQ ID NO: 9); VRLCitSSV (SEQ ID NO: 10); VCitLCitSSV (SEQ ID NO: 11); ESTCitGRS (SEQ ID NO: 12); ESTRGCitS (SEQ ID NO: 13); ESTCitGCitS (SEQ ID NO: 14); CitPAPPP (SEQ ID NO: 15) and ACitGLT (SEQ ID NO: 16) and combinations thereof. Each possibility is a separate embodiment of the invention.

In some embodiments said the synthetic peptide comprises a plurality of arthritic related autoantigen epitopes selected from the group consisting of: VRLRSSV (SEQ ID NO: 5); ESTRGRS (SEQ ID NO: 6); RPAPPP (SEQ ID NO: 7); and ARGLT (SEQ ID NO: 8). Each possibility is a separate embodiment of the invention.

In some embodiments said the synthetic peptide comprises a plurality of arthritic related autoantigen epitopes selected from the group consisting of: VCitLRSSV (SEQ ID NO: 9); VRLCitSSV (SEQ ID NO: 10); VCitLCitSSV (SEQ ID NO: 11); ESTCitGRS (SEQ ID NO: 12); ESTRGCitS (SEQ ID NO: 13); ESTCitGCitS (SEQ ID NO: 14); CitPAPPP (SEQ ID NO: 15) and ACitGLT (SEQ ID NO: 16). Each possibility is a separate embodiment of the invention.

In some embodiments said the synthetic peptide comprises the amino acid sequence set forth in SEQ ID NO: 1, or an analog or derivative thereof. In some embodiments said the synthetic peptide is consisting of the amino acid sequence set forth in SEQ ID NO: 1. A peptide comprising, or consisting of, the amino acid sequence set forth in SEQ ID NO: 1 is also denoted hereinafter "Cit-ME".

In some embodiments said the synthetic peptide comprises the amino acid sequence set forth in SEQ ID NO: 4, or an analog or derivative thereof. In some embodiments said the synthetic peptide is consisting of the amino acid sequence set forth in SEQ ID NO: 4. A peptide comprising, or consisting of, the amino acid sequence set forth in SEQ ID NO: 4 is also denoted hereinafter "Non-Cit-ME".

In some embodiments the present invention provides a synthetic citrullinated peptide comprising at least two citrullinated residues, wherein said peptide is derived from a protein selected from the group consisting of: vimentin, filaggrin, beta-fibrinogen, collagen, α-enolase, fibrinogen-a and aggrecan.

In some embodiments the synthetic citrullinated peptide comprises at least three citrullinated residues.

In some embodiments the synthetic citrullinated peptide is derived from beta-fibrinogen.

In some embodiments the synthetic citrullinated peptide comprises the amino acid sequence CitPAPPPISGGGYCitACit (SEQ ID NO: 2). In some embodiments the synthetic citrullinated peptide is consisting of the amino acid sequence set forth in SEQ ID NO: 2. A peptide comprising, or consisting of, the amino acid sequence set forth in SEQ ID NO: 2 is also denoted hereinafter "β-Fib-Cit".

In some embodiments the synthetic citrullinated peptide is derived from collagen type II.

In some embodiments the synthetic citrullinated peptide comprises the amino acid sequence ACitGLTGCitPGDAK (SEQ ID NO: 21). In some embodiments the synthetic citrullinated peptide is consisting of the amino acid sequence set forth in SEQ ID NO: 21.

Without being bound by any theory or mechanism, the synthetic multiepitope peptide and the synthetic citrullinated peptide modulate the immune response in a subject in need thereof, for example by inducing the production of anti-inflammatory cytokines, inhibiting the production of pro-inflammatory cytokines, increasing T-regulatory cell population, decreasing IL-17 positive cell population and any combination thereof. Each possibility is a separate embodiment of the invention.

As used herein a "Regulatory T cell population" refers to a T cell population expressing CD4, CD25 and FoxP3.

As used herein an "inflammatory T cell population" and a "Th17 T cell population" interchangeably refer to a T cell population expressing IL-17.

Typically, immune tolerance re-establishment in autoimmune diseases is based on repairing a pro-/anti-inflammatory imbalance of T cell subpopulations. IL-17-producing T (Th17) cells have a crucial role in the induction of autoimmune tissue injury. In contrast, Regulatory T cells, defined by the expression of CD4, CD25 and the transcription factor FoxP3, have been shown to be essential for controlling autoimmunity, leading to peripheral tolerance.

The term "autoimmune disease" as used herein refers to diseases and disorders induced by the body's immune responses being directed against its own tissues, causing prolonged inflammation and subsequent tissue destruction. Non limiting examples of autoimmune diseases and disorders include alopecia areata, diabetes Type 1, Guillain-Barre syndrome, multiple sclerosis, rheumatoid arthritis and systemic lupus erythematosus among others.

As used herein "rheumatoid arthritis" refers to a chronic, systemic inflammatory disorder that may affect many tissues and organs, but principally attacks flexible (synovial) joints.

In some embodiments, the present invention provides a method of treating an autoimmune disease or disorder comprising administering to a subject in need thereof a therapeutically effective amount of a pharmaceutical composition comprising a synthetic peptide and a pharmaceutically acceptable carrier, wherein said peptide comprises a plurality of epitopes, each epitope being derived from a different protein, and wherein at least one epitope comprises arginine or a citrullinated residue.

In some embodiments, the protein is selected from the group consisting of: vimentin, filaggrin, beta-fibrinogen, collagen, α-enolase, fibrinogen-a, aggrecan and any combination thereof. Each possibility is a separate embodiment of the invention.

In some embodiments said synthetic peptide comprises the amino acid sequence set forth in SEQ ID NO: 1. In some embodiments said synthetic peptide comprises the amino acid sequence set forth in SEQ ID NO: 4. In some embodiments said synthetic peptide comprises the amino acid sequence set forth in SEQ ID NO: 5. In some embodiments said synthetic peptide comprises the amino acid sequence set forth in SEQ ID NO: 6. In some embodiments said synthetic peptide comprises the amino acid sequence set forth in SEQ ID NO: 7. In some embodiments said synthetic peptide comprises the amino acid sequence set forth in SEQ ID NO: 8. In some embodiments said synthetic peptide comprises the amino acid sequence set forth in SEQ ID NO: 9. In some embodiments said synthetic peptide comprises the amino acid sequence set forth in SEQ ID NO: 10. In some embodiments said synthetic peptide comprises the amino acid sequence set forth in SEQ ID NO: 11. In some embodiments said synthetic peptide comprises the amino acid sequence set forth in SEQ ID NO: 12. In some embodiments said synthetic peptide comprises the amino acid sequence set forth in SEQ ID NO: 13. In some embodiments said synthetic peptide comprises the amino acid sequence set forth in SEQ ID NO: 14. In some embodiments said synthetic peptide comprises the amino acid sequence set forth in SEQ ID NO: 15. In some embodiments said synthetic peptide comprises the amino acid sequence set forth in SEQ ID NO: 16.

In some embodiments, the present invention provides a method of treating an autoimmune disease comprising administering to a subject in need thereof a therapeutically effective amount of a pharmaceutical composition comprising a synthetic citrullinated peptide and a pharmaceutically acceptable carrier, wherein said synthetic citrullinated peptide comprises at least two citrullinated residues, and wherein said peptide is derived from a protein selected from the group consisting of: vimentin, filaggrin, beta-fibrinogen, collagen, α-enolase, fibrinogen-a and aggrecan.

In some embodiments the present invention provides a pharmaceutical composition comprising a synthetic citrullinated peptide and a pharmaceutically acceptable carrier for use in the treatment of an autoimmune disease or disorder, wherein said synthetic citrullinated peptide comprises at least two citrullinated residues, and wherein said peptide is derived from a protein selected from the group consisting of: vimentin, filaggrin, beta-fibrinogen, collagen, α-enolase, fibrinogen-a and aggrecan.

In some embodiments said synthetic peptide comprises the amino acid sequence set forth in SEQ ID NO: 2. In some embodiments said synthetic peptide comprises the amino acid sequence set forth in SEQ ID NO: 21.

In some embodiments the disease is rheumatoid arthritis.

In some embodiments treatment comprises reducing the symptoms associated with said autoimmune disease or disorder, reducing the severity of said autoimmune disease or disorder, ameliorating said autoimmune disease or disorder, inhibiting further progression of said autoimmune disease or disorder, curing said autoimmune disease or disorder and any combination thereof.

In some embodiments treatment a subject in need of treatment is a patient having rheumatoid arthritis, a patient having rheumatoid arthritis in remission, a patient with rheumatoid arthritis wherein the patient has manifested rheumatoid arthritis symptoms and a patient susceptible to RA. Each possibility is a separate embodiment of the invention.

As used herein "remission in rheumatoid arthritis" refers to the absence of clinical signs of inflammation. It is understood by the skilled in the art that only a very small percentage of patients are able to discontinue their arthritis medications, where usually more than 95% need to continue on their medication to remain in remission.

As used herein a patient with "manifested rheumatoid arthritis symptoms" refer to a patient suffering from a symptom selected from the group consisting of: tender, warm, swollen joints, long lasting morning stiffness, rheumatoid nodules, fatigue, fever and weight loss and combinations thereof. Each possibility is a separate embodiment of the invention.

As used herein the expression "a patient susceptible to RA" is interchangeable with "a subject prone to development of RA", "a subject prone to occurrence of RA", and "a subject having an increased susceptibility to RA" and refers to a subject having genetic makeup which enhances the chance of the subject to show symptoms of RA.

In some embodiments the present invention provides a pharmaceutical composition comprising a synthetic peptide and a pharmaceutically acceptable carrier, wherein said peptide comprises a plurality of epitopes, each epitope being derived from a protein selected from the group consisting of: vimentin, filaggrin, beta-fibrinogen, collagen, α-enolase, fibrinogen-a, aggrecan and any combination thereof, and wherein at least one epitope comprises at least one arginine or at least one citrullinated residue.

In some embodiments, the synthetic peptide comprises at least one additional arginine residue adapted to be citrullinated upon administration.

In some embodiments the synthetic peptide comprises at least three epitopes. In some embodiments each epitope of said plurality of epitopes is derived from a different protein. In some embodiments said synthetic peptide comprises the amino acid sequence set forth in SEQ ID NO: 1. In some embodiments said synthetic peptide comprises the amino acid sequence set forth in SEQ ID NO: 4.

The compositions described herein may be prepared by known methods for the preparation of pharmaceutically acceptable compositions intended for administration to a subject, such that an effective quantity of the active substance (i.e. peptide) is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water. Other carriers may be, for example MHC class II molecules. Soluble MHC class II molecules including monomers, dimers, trimers, tetramers, etc, as well as citrulline peptide/MHC class II complexes can be made by methods disclosed in U.S. Pat. No. 5,869,270.

Furthermore the pharmaceutical composition according to the invention may comprise one or more stabilizers such as, for example, carbohydrates including sorbitol, mannitol, starch, sucrose, dextrin and glucose, proteins such as albumin or casein, and buffers like alkaline phosphates.

The pharmaceutical composition of the invention may also comprise one or more adjuvants. As is well known to those of ordinary skill in the art, the ability of an immunogen to induce/elicit an immune response can be improved if, regardless of administration formulation (i.e. recombinant virus, nucleic acid, peptide), the immunogen is co-administered with an adjuvant. Adjuvants typically enhance the immunogenicity of an immunogen but are not necessarily immunogenic in and of themselves. Adjuvants may act by retaining the immunogen locally near the site of administration to produce a depot effect facilitating a slow, sustained release of immunizing agent to cells of the immune system. Adjuvants can also attract cells of the immune system to an immunogen depot and stimulate such cells to elicit immune responses. As such, embodiments of this invention encompass compositions further comprising adjuvants.

Suitable adjuvants include, amongst others, aluminium hydroxide, aluminium phosphate, amphigen, tocophenols, monophosphenyl lipid A, muramyl dipeptide and saponins such as Quill A. Preferably, the adjuvants to be used in the tolerance therapy according to the invention are mucosal adjuvants such as the cholera toxine B-subunit or carbomers, which bind to the mucosal epithelium. The amount of adjuvant depends on the nature of the adjuvant itself as is understood by one of skill in the art.

In some embodiments, the present invention provides a pharmaceutical composition comprising a synthetic citrullinated peptide and a pharmaceutically acceptable carrier, wherein said peptide comprises at least two citrullinated residues, and wherein said peptide being derived from a protein selected from the group consisting of: vimentin, filaggrin, beta-fibrinogen, collagen, α-enolase, fibrinogen-a and aggrecan.

In some embodiments said synthetic citrullinated peptide comprises at least three citrullinated residues. In some embodiments said synthetic citrullinated peptide comprises the amino acid sequence CitPAPPPISGGGYCitACit (SEQ ID NO: 2). In some embodiments said synthetic citrullinated peptide comprises the amino acid sequence ACitGLTGCit-PGDAK (SEQ ID NO: 21).

In some embodiments said synthetic peptide comprises the amino acid sequence set forth in SEQ ID NO: 1. In some embodiments said synthetic peptide comprises the amino acid sequence set forth in SEQ ID NO: 4.

As a non-limiting example, the pharmaceutical composition of the invention may be administered to a rheumatoid arthritis patient who is currently in remission in order inhibit reinstatement of the disease or to inhibit further progression of the disease. As another non-limiting example, the pharmaceutical composition may be administered to a rheumatoid arthritis patient with manifested rheumatoid arthritis symptoms in order to reduce the severity of rheumatoid arthritis in the subject. As another non-limiting example, the pharmaceutical composition may be administered to a rheumatoid arthritis patient with manifested rheumatoid arthritis symptoms in order to ameliorate the symptoms of rheumatoid arthritis. As another non-limiting example, the pharmaceutical composition may be administered to a rheumatoid arthritis patient with manifested rheumatoid arthritis symptoms in order to inhibit further progression of rheumatoid arthritis. As another non-limiting example, the pharmaceutical composition may be administered to a rheumatoid arthritis patient with manifested rheumatoid arthritis symptoms in order to cure rheumatoid arthritis. As another non-limiting example, the pharmaceutical composition may be administered to a patient diagnosed with rheumatoid arthritis in order to prevent the manifestation of rheumatoid arthritis symptoms.

As used herein a patient "diagnosed with rheumatoid arthritis" refers to a patient in whom anti-citrullinated proteins antibodies are detected. It is understood by the skilled in the art that anti-citrullinated antibodies may be detected even before the onset of the disease symptoms.

In some embodiments, administering the pharmaceutical composition comprises administering via a route selected from the group consisting of: subcutaneous, topical, transdermal, oral, buccal, sublingual, sublabial, intradermal, or combinations thereof. Each possibility is a separate embodiment of the invention.

Administration of "a therapeutically active amount" of the pharmaceutical compositions of the present invention, or an "effective amount", refers to administration of an amount effective at dosages and for periods of time, necessary to elicit a desired therapeutic response in a human. A therapeutically effective amount of a substance may vary according to factors such as the disease state/health, age, sex, and weight of the recipient, and the inherent ability of the particular peptide to elicit a desired immune response. Dosage regimes may be adjusted to provide the optimum therapeutic response. For example, several divided doses may be administered daily or on at periodic intervals, and/or the dose may be proportionally reduced as indicated by the exigencies of the therapeutic situation. The amount of peptide for administration will depend on the route of administration, time of administration and varied in accordance with individual subject responses.

The peptides of the present invention may be made by methods known to those of skill in the art most notably and preferably by chemical synthesis using techniques well known in the chemistry of proteins such as solid phase synthesis or synthesis in homogenous solution to generate synthetic peptides. Citrulline, which is a post-translationally modified arginine may be created artificially, through deimination, a process which is catalyzed by the enzyme peptidylarginine deiminase. During the process, a positive charge is removed from arginine thereby resulting with citrulline which is polar in nature.

In some embodiments, the peptides of the invention may be made from known commercially available sources of suitable proteins, such as, for example filaggrin, beta-Fibrinogen, vimentin, collagen, α-enolase, fibrinogen-a and aggrecan. In this respect, citrullinated peptides may be synthesized from lyophilized proteins reconstituted in an appropriate buffer to which the enzyme peptidylarginine deiminase is added. The solution is allowed to stand at an appropriate temperature for a time sufficient to cause modification of arginine residues to citrulline and thus create citrullinated proteins or peptides. The citrullinated proteins are then isolated by the removal of the enzyme using a high molecular weight membrane or other methods of chromatography. One of skill in the art will understand that the temperature of incubation, buffer condition and time of incubation may vary depending on the protein that is being deiminated.

The multiepitope peptides and the citrullinated peptides may be isolated and purified by methods selected on the basis of properties revealed by their sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chromatography) or by precipitation (immunoprecipitation). Polyacrylamide gel electrophoresis can also be used to isolate the citrullinated proteins based on the molecular weight of the protein, charge properties and hydrophobicity. The purified peptides can be used in further biochemical analyses to establish secondary and tertiary structure which may aid in the design of pharmaceuticals to interact with the protein, alter the peptide's charge configuration or charge interaction with other proteins or peptides, or alter its function.

According to alternative embodiments, the peptides of the invention may be produced by the use of recombinant DNA techniques as are well known to one skilled in the art. With reference to the citrullinated peptides, as citrulline is not encoded by any trinucleotide sequence, a nucleic acid sequence encoding for arginine may be used with the resultant protein sequence being modified using peptidylarginine deiminase to convert an arginine to citrulline. It is further within the scope of the invention to use a nucleic acid sequence encoding for glutamine, an amino acid that resembles citrulline. In this manner, a naturally occurring sequence that contains arginine can be used in which the arginine is substituted with glutamine in order to resemble citrulline. Nucleic acid sequences which encode for the selected peptides of the invention may be incorporated in a known manner into appropriate expression vectors (i.e. recombinant expression vectors). Possible expression vectors include (but are not limited to) cosmids, plasmids, or modified viruses (e.g. replication defective retroviruses, adenoviruses and adeno-associated viruses, lentiviruses, herpes viruses, poxviruses), so long as the vector is compatible with the host cell used. The expression "vector . . . compatible with the host cell" is defined as contemplating that the expression vector(s) contain a nucleic acid molecule of the invention and attendant regulatory sequence(s) selected on the basis of the host cell(s) to be used for expression, said regulatory sequence(s) being operatively linked to the nucleic acid molecule. "Operatively linked" is intended to mean that the nucleic acid is linked to regulatory sequence(s) in a manner which allows expression of the nucleic acid. Suitable regulatory sequences may be derived from a variety of sources, including bacteria, fungal, or viral genes (for example, see the regulatory sequences described in Goeddel, Gene Expression Technology: Methods in Enzymology 185, Academic Press, San Diego, Calif. (1990)). Selection of appropriate regulatory sequence(s) is dependent on the host cell(s) chosen, and may be readily accomplished by one of ordinary skill in the art. Examples of such regulatory sequences include the following: a transcriptional promoter and enhancer, RNA polymerase binding sequence, or a ribosomal binding sequence (including a translation initiation signal). Depending on the host cell chosen and the expression vector employed, other additional sequences (such as an origin of replication, additional DNA restriction sites, enhancers, and sequences conferring inducibility of transcription) may be incorporated into the expression vector.

The peptides of the invention may also be produced recombinantly in association with a soluble MHC molecule using a variety of methods known to those of skill in the art. Methods for making peptide/MHC class II soluble complexes are also provided in U.S. Pat. No. 5,869,279.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1: The Effect of Fil-Cit and β-Fib-Cit Peptides on Gene Expression in Peripheral Blood Mononuclear Cells of RA Patients Citrullinated peptide derived from filaggrin, set forth in SEQ ID NO: 3, (HQCHQESTCitGRSRGRCGRSGS) designated Fil-Cit and citrullinated peptide derived from β-fibrinogen sequence (designated β-Fib-Cit) set forth in SEQ ID NO: 2 (CitPAPPPISGGGYCitACit) were examined for their ability to immunomodulate cytokine expression in peripheral blood mononuclear cells from rheumatoid arthritis patients. Matched non-citrullinated forms of those peptides served as control, and were designated Fil-NC and β-Fib-NC, respectively. All rheumatoid arthritis patients who participated in the study signed an informed consent and the research was approved by the Sheba Helsinki committee (approval No 9247-12-SMC). All procedures were conducted according to good clinical practice (GCP) regulations. All rheumatoid arthritis patients selected for this study, were either newly diagnosed or in a remission stage and did not receive treatment at the time blood or synovial fluid samples were taken.

Figure 1B:
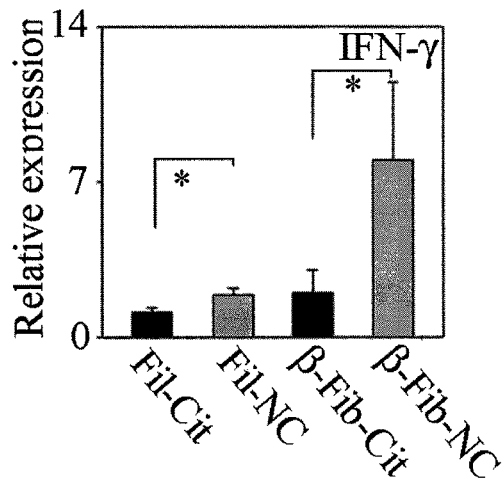
Figure 1C:
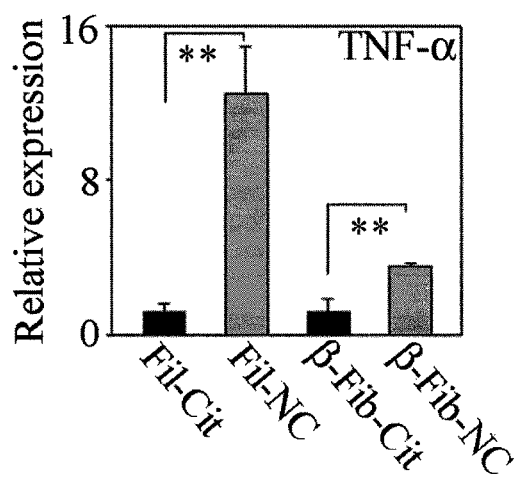
Figure 1D:
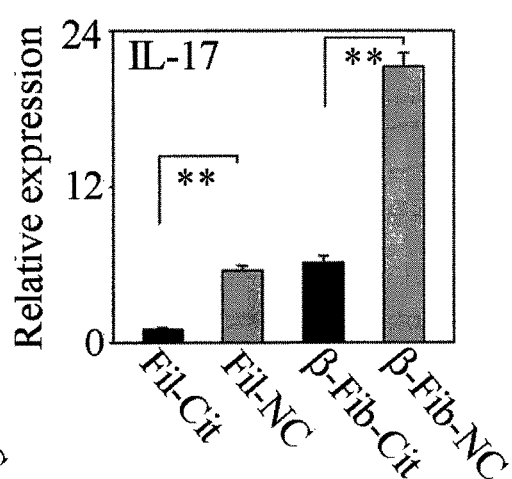

Peripheral blood mononuclear cells were isolated from blood samples using Ficoll-Paque density gradient centrifugation. The extracted cells were cultivated in the presence of Fil-Cit (0.25 μg/ml or 1.25 μg/ml), β-Fib-Cit (0.25 μg/ml or 1.25 μg/ml) and the control matched peptides. Total RNA was extracted 24 h after incubation with the peptides. Incubation of the cells with the peptides resulted in the immunomodulation of TGF-β, IFN-γ, TNF-α, and IL-17 genes, determined by real-time PCR. As shown in FIG. 1A, following incubation with Fil-Cit or β-Fib-Cit, the levels of the anti-inflammatory TGF-β gene expression were significantly up-regulated as compared with their levels following incubation with the control non-citrullinated peptides. The levels of the pro-inflammatory IFN-γ, TNF-α and IL-17 (FIGS. 1B-1D, respectively) were down-regulated (*p≤0.05, **p≤0.007).

Figure 2:
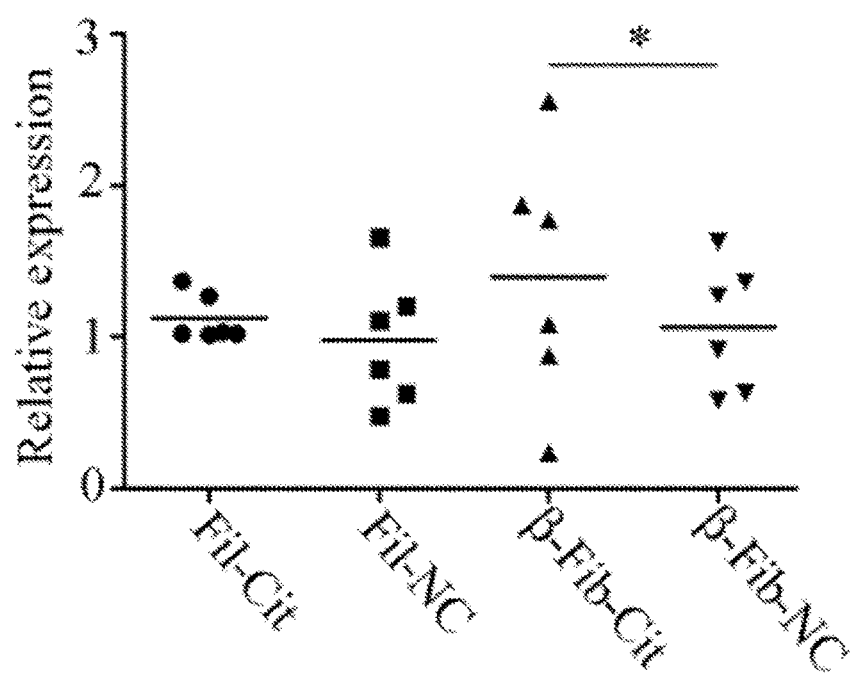
FIG. 2 shows TGF-β gene expression level in peripheral blood mononuclear cells derived from rheumatoid arthritis patients cultured in the presence of Fil-Cit, Fil-NC, β-Fib-Cit and β-Fib-NC peptides (*p≤0.05).

Example 2: Effect of Fil-Cit and β-Fib-Cit on TGF-β Gene Expression in Peripheral Blood Mononuclear Cells of RA Patients To further investigate the ex vivo effects of the citrullinated peptides on TGF-β expression, peripheral blood mononuclear cells obtained from 6 rheumatoid arthritis patients were cultured in the presence of citrullinated or control peptides. As shown in FIG. 2, the mean expression levels of anti-inflammatory TGF-β were significantly up-regulated in peripheral blood mononuclear cells that were incubated with the β-Fib-Cit as compared to peripheral blood mononuclear cells incubated with β-Fib-NC peptide (*p≤0.05). Up-regulation was likewise indicated in peripheral blood mononuclear cells incubated with Fil-Cit.

Example 3: A Multiepitope Synthetic Peptide

Figure 3:
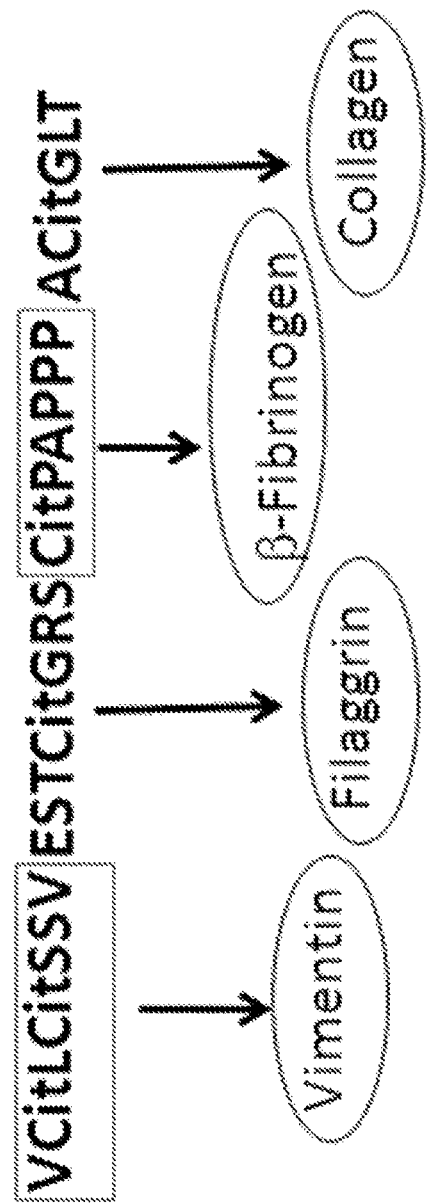
FIG. 3 is a schematic illustration of the peptide set forth in SEQ ID NO: 1 ("Cit-ME").

FIG. 3 is a schematic presentation of the amino acid sequence SEQ ID NO: 1 (VCitLCitSSVESTCitGRSCit- PAPPPACitGLT), a multiepitope peptide derived from four major arthritic related citrullinated autoantigens sequence also termed "Cit-ME". The arrows indicate the arthritic autoantigen target from which the sequence of each epitope was derived. A peptide with a matched sequence in which the citrulline residues are substituted for arginine, having the amino acid sequence set forth in SEQ ID NO: 4, also termed "Non-Cit-ME", was likewise generated.

Example 4: Cit-ME Peptide Reacts with Anti-Citrullinated Protein Antibodies

Figure 4:
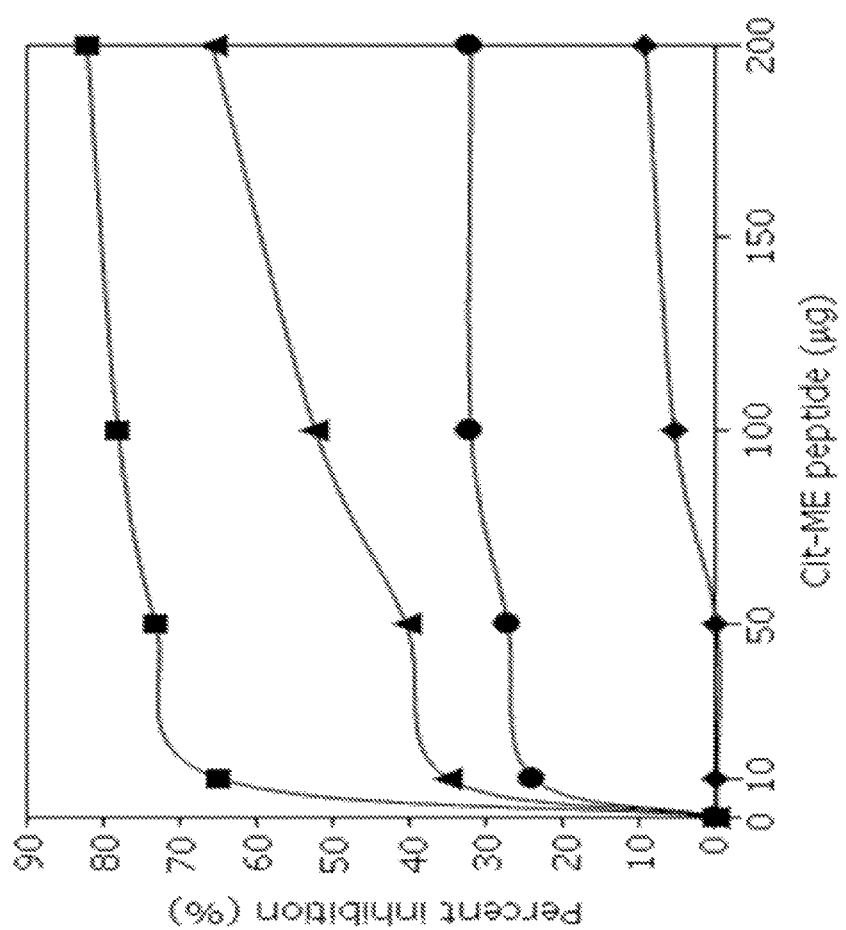
FIG. 4 shows the cross-reactivity of Cit-ME with different specific anti-citrullinated protein antibodies (ACPA): anti-cit filaggrin (square), anti-cit-β-fibrinogen (triangle), anti-cit-collagen (circle) and anti-cit-vimentin (diamond).

Peptide inhibition assay in ELISA was used to confirm the cross-reactivity of the Cit-ME peptide to the following anti-citrullinated protein antibodies (ACPA): anti citrullinated filaggrin, anti cit-β-fibrinogen, anti cit-collagen and anti cit-vimentin. Sera were obtained from ACPA RA patients and samples with highly positive ACPA levels were selected (≥100 U/ml) using commercial CCP ELISA test (INOVA). ELISA test was performed with each of the citrullinated peptides: cit-filaggrin (HQCHQESTCitGRSR-GRCGRSGS) set forth in SEQ ID NO: 3, cit-β-fibrinogen (CitPAPPPISGGGYCitACit) set forth in SEQ ID NO: 2, cit-collagen (ACitGLTGCitPGDAK) set forth in SEQ ID NO: 21 and cit-vimentin (SAVRACitSSVPGVRK) set forth in SEQ ID NO: 22. Sera were diluted in PBS to obtain a reactivity of approximately 50% binding OD under standard assay conditions. Increasing concentrations of Cit-ME peptide were added to the diluted sera and incubated for two hours at room temperature. Specimens were then assayed in ELISA plates coated with each one of the peptides. As shown in FIG. 4, the Cit-ME peptide inhibits the binding of the ACPA. Specifically, 10-200 µg of Cit-ME peptide was sufficient to impair the binding of specific ACPA to cit-filaggrin (FIG. 4, squares), cit-β-fibrinogen (FIG. 4, triangles) and cit-collagen (FIG. 4, circles) and to a lesser extent of cit-vimentin (FIG. 4, diamonds). Thus, ACPA have binding specificity to Cit-ME.

Example 5: TGF-β, TNF-α, and IFN-γ Gene Expression in the Presence of a Cit-ME

To assess the effect of the Cit-ME peptide (SEQ ID NO: 1) on inflammatory related genes expression, peripheral blood mononuclear cells derived from synovial fluid rheumatoid arthritis patients were incubated with the Cit-ME multi-epitope citrullinated peptide for 24 h. The effect of the peptide on gene expression was compared also to the effect of infliximab, a TNF-α blocker, which is an antirheumatic drug that acts as an anti-inflammatory compound. As shown in FIGS. 5A-5C, Cit-ME up-regulated the expression of TGF-β (FIG. 5A), an anti-inflammatory gene, while down-regulated the TNF-α, and IFN-γ pro-inflammatory genes (FIGS. 5B-5C, respectively) compared to the non-citrullinated peptides. Results were determined by real-time PCR. The expression level of the TNF-α was downregulated in the presence of Infliximab, compared to medium alone (control).

Example 6: Effect of Citrullinated Peptides on Regulatory T Cells

Figure 6A:
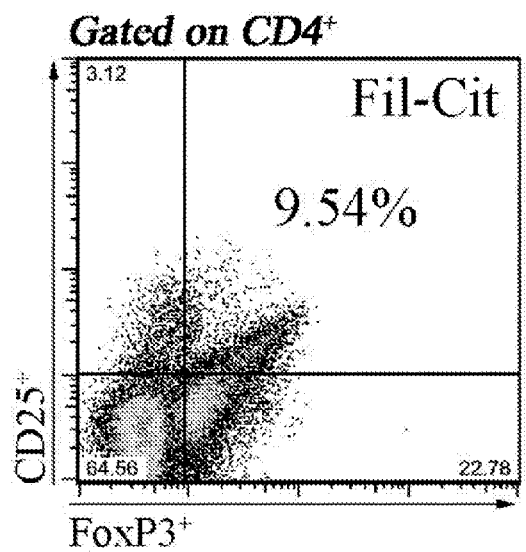
FIG. 6 are FACS two dimensional dot plots of regulatory T cells from rheumatoid arthritis patients, incubated with the citrullinated peptides Fil-Cit (A), β-Fib-Cit (B), Non-Cit-Fil (C), Non-Cit-β-Fib (D), Cit-ME (E), Infliximab (F), Non-Cit-ME (G) and medium (untreated; H).
Figure 6B:
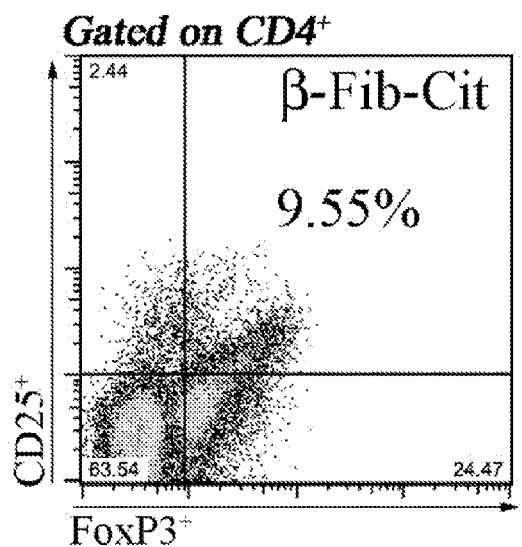
Figure 6C:
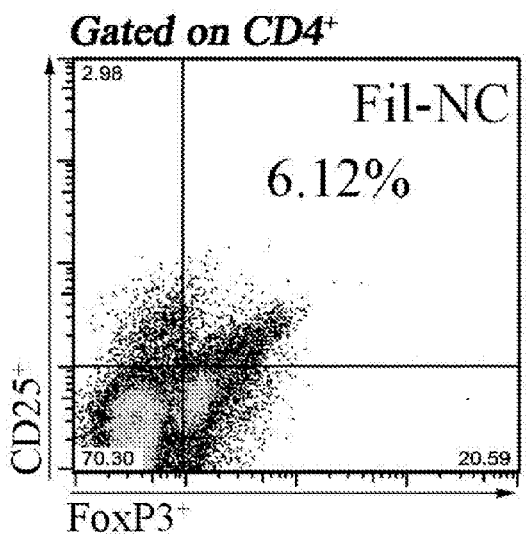
Figure 6D:
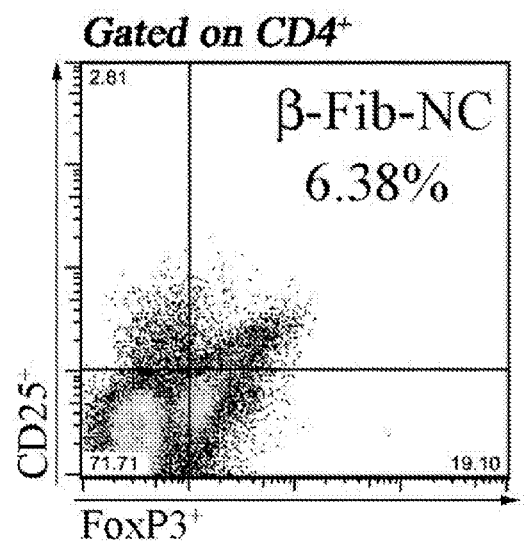
Figure 6E:
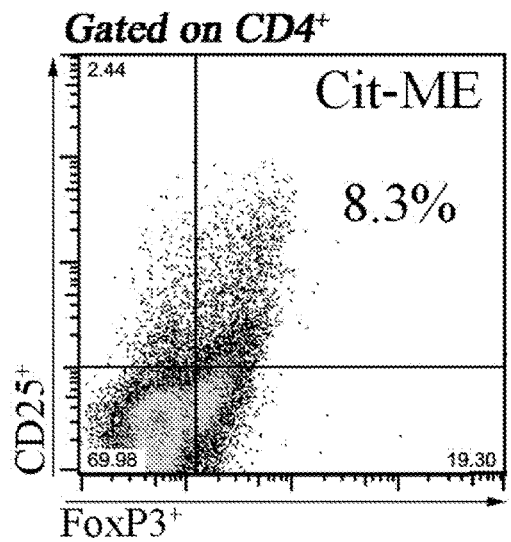
Figure 6F:
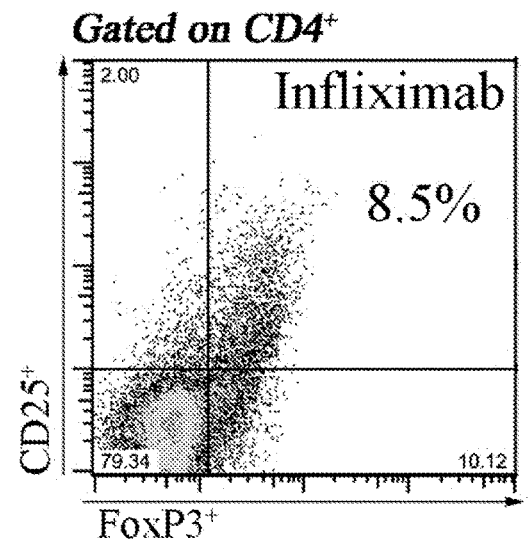
Figure 6G:
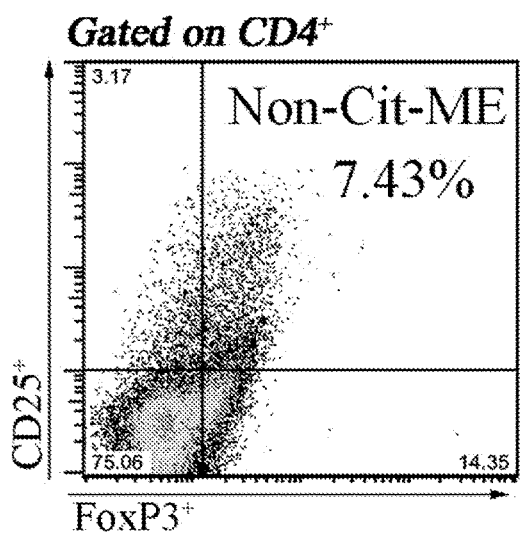
Figure 6H:
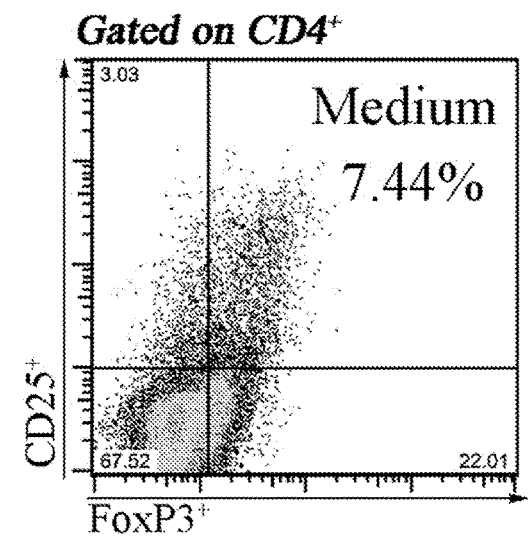

Given the observed immunomodulation of cytokines following incubation of peripheral blood mononuclear cells obtained from rheumatoid arthritis patients with citrullinated peptides, the citrullinated peptides were tested for their ability to exert an effect on the T regulatory population proportion. Peripheral blood mononuclear cells of rheumatoid arthritis patients were cultured in the presence of 1.25 µg/ml of the peptides (Fil-Cit, β-Fib-Cit, and Cit-ME; FIGS. 6A, 6B and 6E, respectively, and Fil-NC, β-Fib-NC and Non-Cit-ME; FIGS. 6C, 6D and 6G, respectively), and Infliximab (FIG. 6F) for 48 hours. Cells cultured with medium devoid of the peptides and Infliximab served as control (FIG. 6H). Thereafter, cells were stained for the expression of CD4, CD25, and FoxP3 and analyzed by FACS. As can be seen in FIGS. 6A-6H, significant up-regulation in the mean percentage of $CD4^+CD25^+Foxp3^+$ T cells was detected following incubation with the citrullinated peptides: increase of 56% (Fil-Cit; FIG. 6A), 50% (β-Fib-Cit; FIG. 6B), and 12% (Cit-ME; FIG. 6E) as compared with the non-citrullinated matched peptides (FIGS. 6C, 6D, and 6G). Mean percentage of $CD4^+CD25^+Foxp3^+$ T cells in the presence of Infliximab was increased by 14% as compared to medium (FIG. 6F and FIG. 6H, respectively). Thus, citrullinated peptides are able to induce the expansion of the T regulatory cell population.

Example 7: Effect of Citrullinated Peptides on Pathogenic Th17 Cells

Figure 7E:
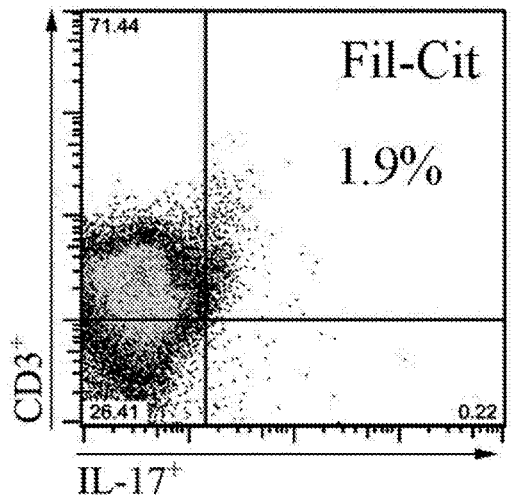
FIG. 7 are FACS two dimensional dot plots of IL-17$^+$ T cells subpopulation in peripheral blood mononuclear cells of rheumatoid arthritis patients incubated with Non-Cit-Fil (A), Non-Cit-β-Fib (B), Non-Cit-ME (C), medium (D), Fil-Cit (E), β-Fib-Cit (F), Cit-ME (G) and Infliximab (H).
Figure 7F:
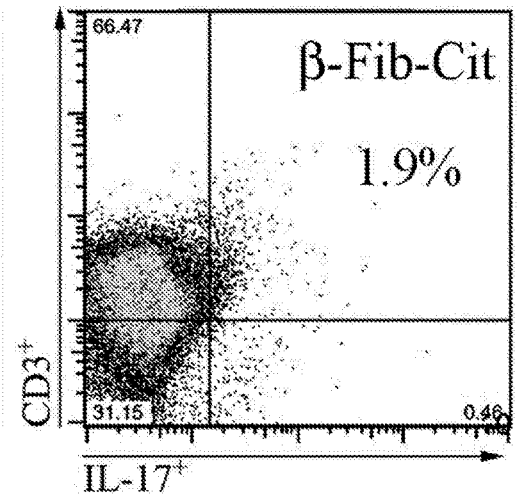
Figure 7G:
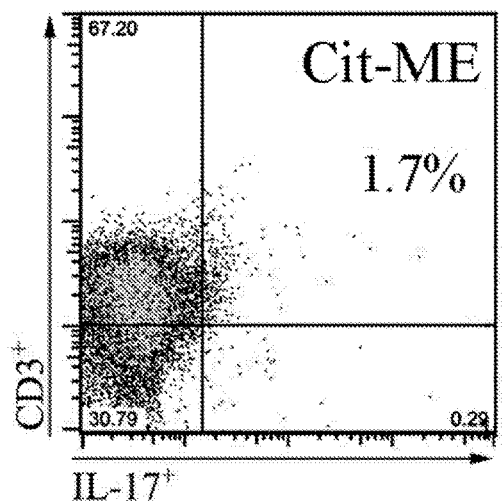
Figure 7H:
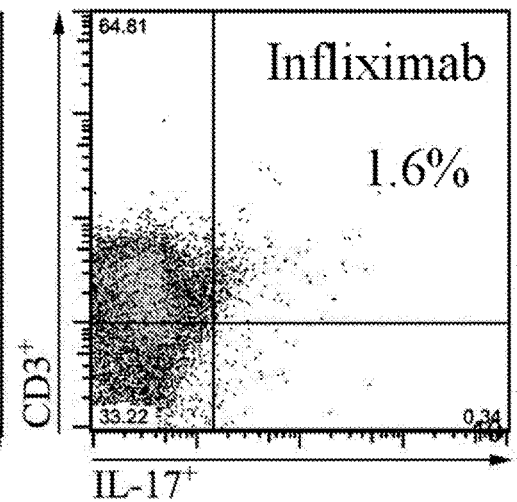

To assess ability of the citrullinated peptides to affect the pathogenic Th17 cells population proportion, peripheral blood mononuclear cells of rheumatoid arthritis patients were cultured in the presence of citrullinated peptides, non-citrullinated peptides and Infliximab for 48 hours. In the last 4 hours phorbol12-myristate 13-acetate (PMA), ionomycin and brefeldin A were added to the culture. Thereafter cells were stained with antibodies against CD3 and IL-17. As shown in FIGS. 7A-7H, significant down-regulation in the mean percentage of pathogenic Th17 cells was detected following incubation with the citrullinated peptides: decrease of 21% (Fil-Cit; E), 5% (β-Fib-Cit; F), and 26% (Cit-ME; G) as compared with the non-citrullinated matched peptides (FIG. 7A-7C, respectively). Mean percentage of pathogenic Th17 cells in the presence of Infliximab was decreased by 48% (FIG. 7H) as compared to medium (FIG. 7D). Thus, the proportion of the pathogenic Th17 cells was down-regulated in the presence of the citrullinated peptides.

Example 8: The Effect of the Artificial Peptides on T Cells Apoptosis

Figure 8A:
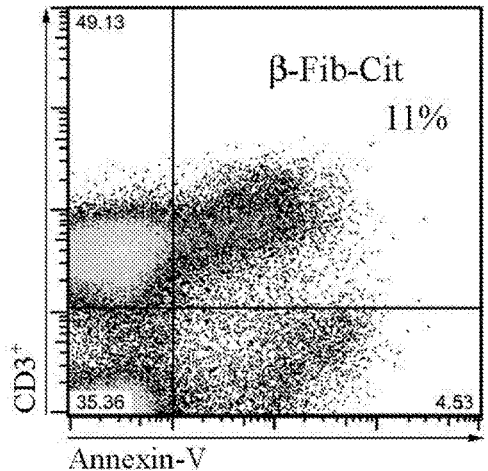
FIG. 8 are FACS two dimensional dot plots of peripheral blood mononuclear cells of rheumatoid arthritis patients cultured in the presence of β-Fib-Cit (A), Cit-ME (B), Infliximab (C), Non-Cit-β-Fib (D), Non-Cit-ME (E) and control cells (medium only; F) and double-stained for annexin V-fluorescein isothiocyanate (FITC) and PI-PE (apoptosis/necrosis markers).
Figure 8B:
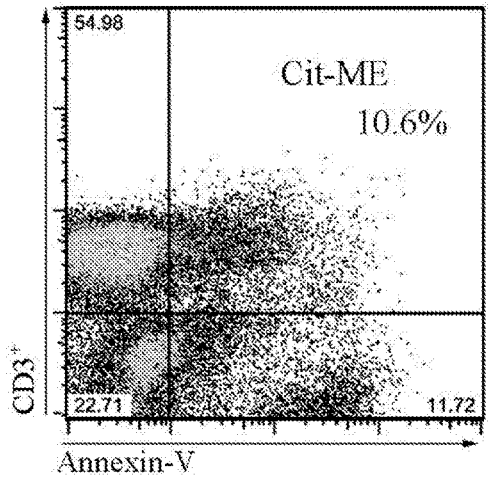
Figure 8C:
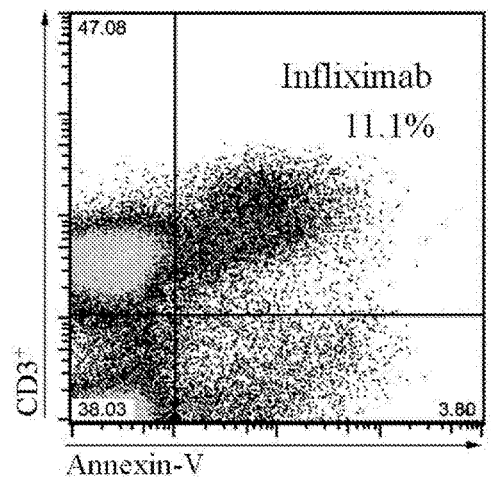
Figure 8D:
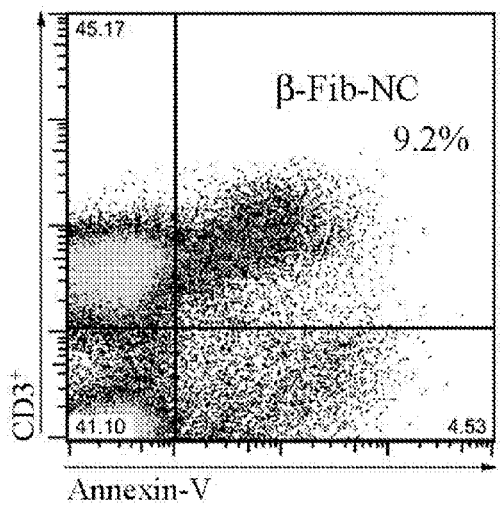
Figure 8E:
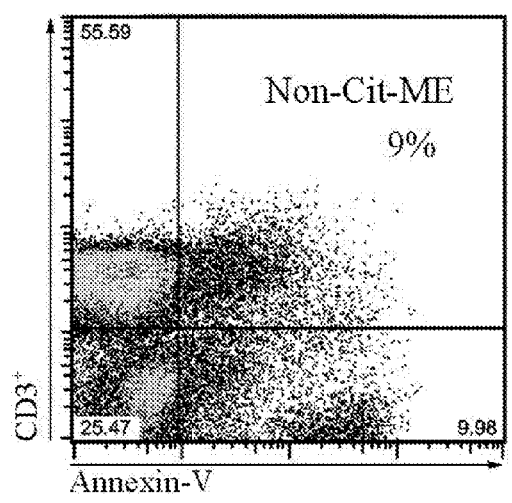
Figure 8F:
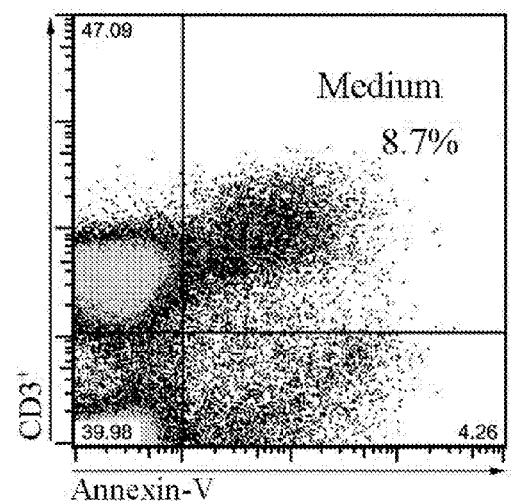

To assess the ability of the citrullinated peptides to affect T cells apoptosis, peripheral blood mononuclear cells of rheumatoid arthritis patients were cultured in the presence of citrullinated, non-citrullinated peptides and Infliximab for 24 hours. Cells were double-stained for annexin V-fluorescein isothiocyanate (FITC) and PI-PE (apoptosis/necrosis markers) and analyzed by FACS. The results in FIG. 8 are presented after gating for PI negative cells (live cells). The β-Fib-Cit and Cit-ME (FIGS. 8A and 8B, respectively) induced T cells apoptosis (by 20% and 18%, respectively) as compared with the non-citrullinated peptides Non-Cit-β-Fib (FIG. 8D) and Non-Cit-ME (FIG. 8E). Infliximab induced apoptosis by 28% (FIG. 8C) as compared with the medium control (FIG. 8F). The results suggest that enhanced T cells apoptosis contribute to the reduced autoimmune response mediated by the citrullinated peptides.

Example 9: The Effect of the Artificial Peptides on Arthritis In Vivo

Figure 9A:
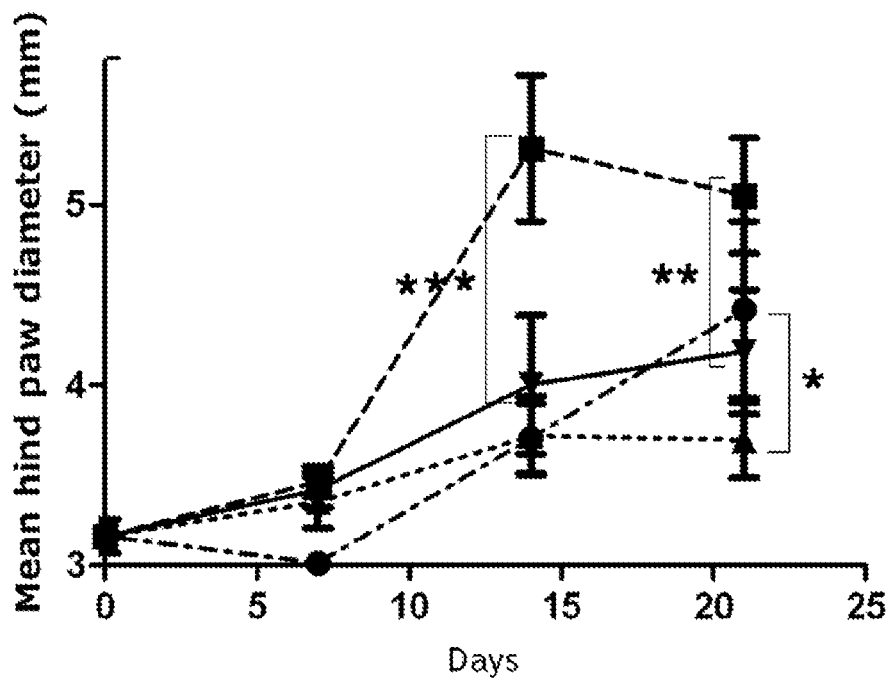
FIG. 9A shows the in vivo effect of Cit-ME (triangle), β-Fib-Cit (circle) and β-Fib-NC (square) in comparison to control (untreated rats; inverted triangle) on mean hind paw diameter of AIA rats (n=5 per treatment; *p≤0.02, p≤0.002, *p≤0.006).

Adjuvant-Induced Arthritis (AIA) was induced in Lewis female rats through immunization with tuberculosis (strain H37Ra) emulsified in incomplete Freund's adjuvant (IFA). Seven days following disease induction rats were assigned into four treatment groups: Cit-ME (FIG. 9A, triangle), β-Fib-Cit (FIG. 9A, circle), β-Fib-NC (FIG. 9A, square) and control (rats undergoing Adjuvant-Induced Arthritis induction without further treatment; FIG. 9A, inverted triangle). Peptides were administered by 10 subcutaneous injections (300 µg/rat) on alternate days. All rats were scored for severity of arthritis, beginning at day 0 for baseline evaluation, for a period of 21 days post disease induction.

Figure 9B:
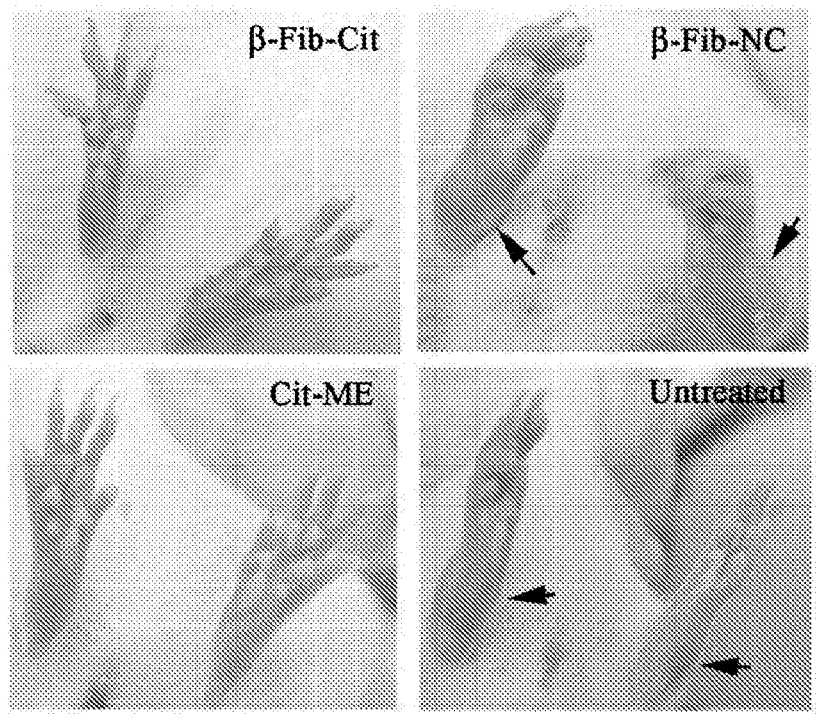
FIG. 9B are photos of hind paws of 4 AIA rats after 27 days treatment with Cit-ME (lower left panel), β-Fib-Cit (upper left panel), β-Fib-NC (upper right panel) in comparison to untreated AIA rat (lower right panel).

Paw swelling measurements were performed by the same observer for all rats, whilst being blinded with regards to which treatment the animal received. Paw swelling was assessed by measuring the mean thickness of the hind limb with a digital micro-caliper. Mean paw swelling is represented by diameter of the average mm paws per rat (n=5) divided by the number of rats per group. Results from 3 independent experiments expressed as mean±SE are presented in FIG. 9A (*p≤0.03). FIG. 9B shows representative images of the left hind paw at day 27 post disease induction and under the aforementioned treatments.

As shown in FIG. 9A, in the non-treated animals (inverted triangle), arthritis symptoms developed gradually and were evident on day 10. In the non-citrullinated peptide treatment group (β-Fib-NC; FIG. 9A, square) severe sign of arthritis were demonstrated and were even higher than the arthritis signs in the non-treated group (FIG. 9A, inverted triangle). Treatment with the Cit-ME peptide resulted in a significant reduced mean paw swelling (circle) compared to the untreated rats or β-Fib-Cit at day 21 post disease induction (as shown in FIG. 9A).

In addition, at day 27 after disease induction, rats treated with the citrullinated peptides showed less symptoms of arthritis (FIG. 9B). The multi-epitope citrullinated peptide (Cit-ME) reduced the arthritis severity as compare to the β-Fib-Cit peptide and to the untreated rats.

Figure 10A:
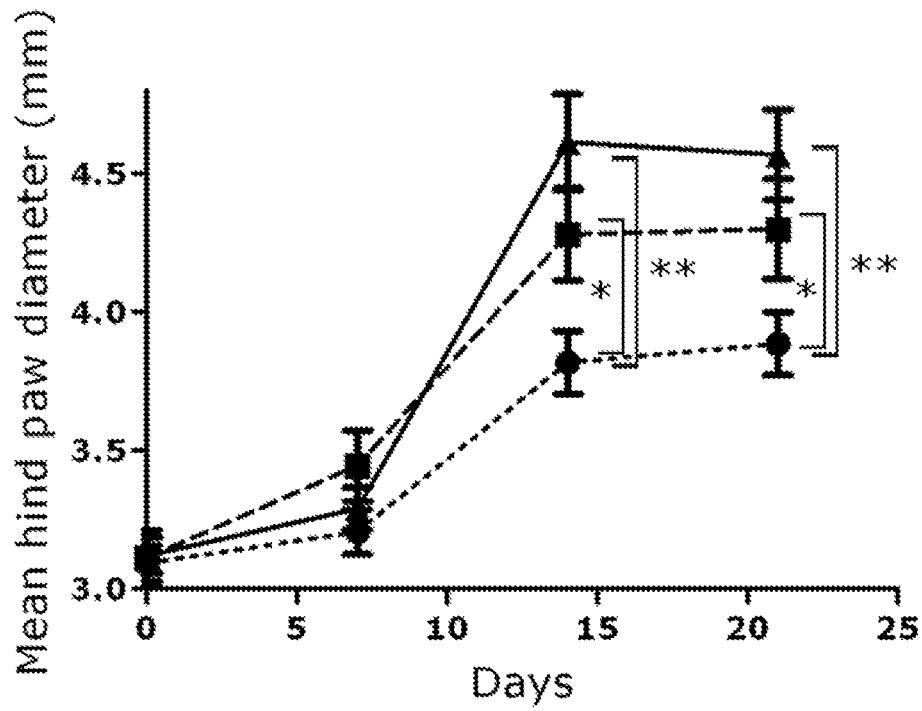
FIG. 10A shows the effect of Cit-ME (circle), Non-Cit-ME (square) and no treatment (triangle) on mean hind paw diameter of AIA rats (*p≤0.03, **p≤0.006).
Figure 10B:
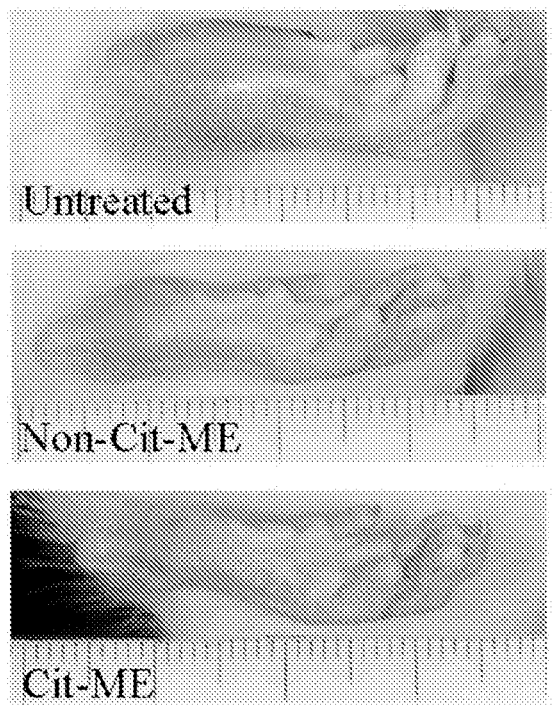
FIG. 10B are photos of a hind paw of 3 AIA rats after 27 days treatment with Cit-ME (lower panel), Non-Cit-ME (middle panel) in comparison to untreated AIA rat (upper panel).

Example 10: The Effect of the Artificial Peptides on Clinical Signs of Arthritis in Rats with Adjuvant Induced Arthritis Clinical signs of arthritis in AIA rats were evaluated as described in Example 9. AIA rats were assigned into three experimental groups: Cit-ME (FIG. 10A, circle), Non-Cit-ME (FIG. 10A, square) and control/untreated (rats undergoing Adjuvant-Induced Arthritis induction without further treatment; FIG. 10A, triangle). Peptides were administered via 8 subcutaneous injections (300 µg per rat) on alternate days starting at day 7 post arthritis induction. Results from 3 independent experiments expressed as mean±SE are presented in FIG. 10A (*p≤0.03, **p≤0.006). Arthritis symptoms developed gradually in the non-treated animals, and were evident on day 10 (FIG. 10A, triangle). The highest severity score was observed on day 14 post induction (FIG. 10A, triangle—4.61±0.17 mean paw diameter). Following treatment with Cit-ME peptide (FIG. 10A, circle), a significant reduction in paw diameter was observed, reaching a maximum value of only 3.81±0.11 (p<0.006). Reduction in clinical score post immunization was also observed following treatment with Non-Cit-ME peptide (FIG. 10A, square). Representative images taken on day 27 reflect the therapeutic effect of the peptides relative to control (FIG. 10B).

Without being bound by any theory or mechanism, the therapeutic effect exerted by Non-Cit-ME may be attributed to citrullination of Arginine residues in-vivo, post injection.

Figure 11A:
FIG. 11 shows histological sections from the ankle joint of AIA rats after 28 days treatment with Cit-ME (A), Non-Cit-ME (B) and no treatment (C) and the corresponding infiltration index (D; Cit-ME, n=11; Non-Cit-ME, n=7; untreated, n=12) (*p<0.01 for Cit-ME-vs. untreated).
Figure 11B:
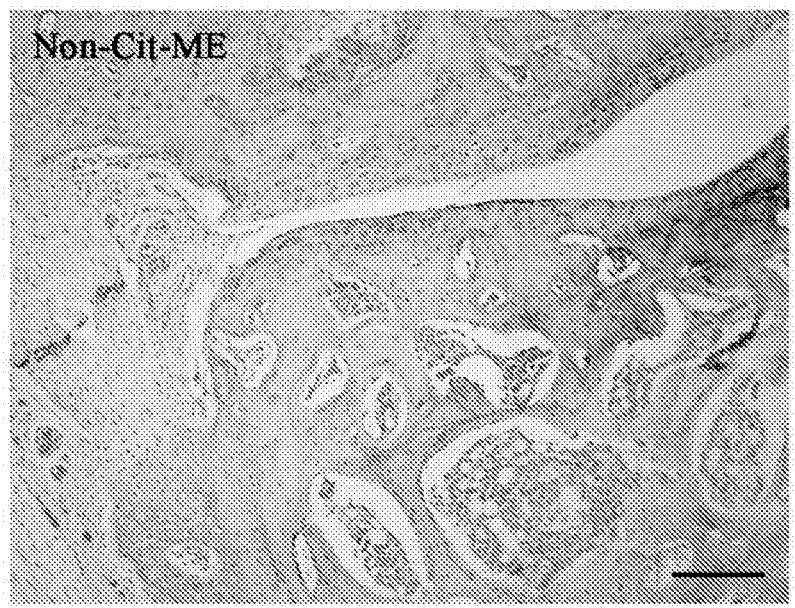
Figure 11C:
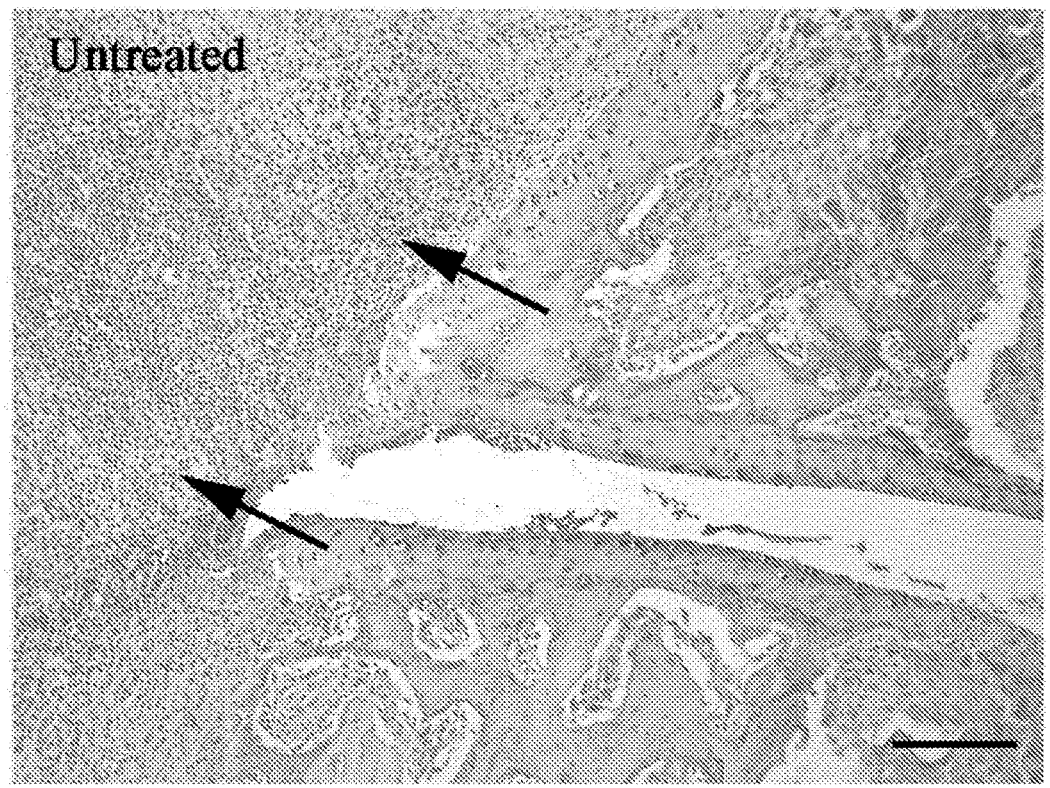
Figure 11D:
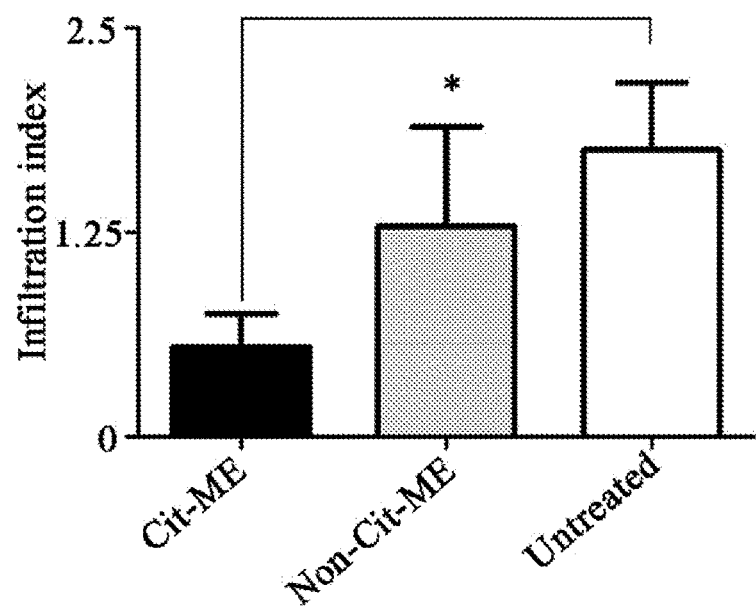

To evaluate the histological signs of arthritis, rats were sacrificed and ankle joints were collected on day 28 post disease induction. The joints were fixed immediately for 24 hours in 4% paraformaldehyde, then decalcified in rapid bone decalcifier (RDO; Apex Engineering, Plainfield, Ill., USA) for 6 hours at room temperature, and further fixed in 4% paraformaldehyde before embedding in paraffin. Sections (5 µm thick) were rehydrated in a graded ethanol series and stained with haematoxylin & eosin (H&E). FIGS. 11A to 11C show representative H&E stained joint tissue sections (magnification ×100). Arrowheads denote the infiltrated zones, scale bar=200 µm. The specimens were scored for severity of inflammation in the synovium, pannus formation, cartilage, and bone erosion. A close correlation between the clinical signs and the histopathological findings was found. As shown in FIG. 11D, Arthritic rats without treatment (n=12) presented a high histological inflammatory score (1.75±0.41), treatment with the Non-Cit-ME peptide (n=7) resulted in a score of 1.28±0.6, whereas rats treated with the Cit-ME peptide (n=12) presented a significantly reduced inflammatory score (0.54±0.2; *p<0.01 for Cit-ME vs. untreated rats).

Example 11: Effect of Cit-ME and Non-Cit-ME on Regulatory T Cells

Figure 12A:
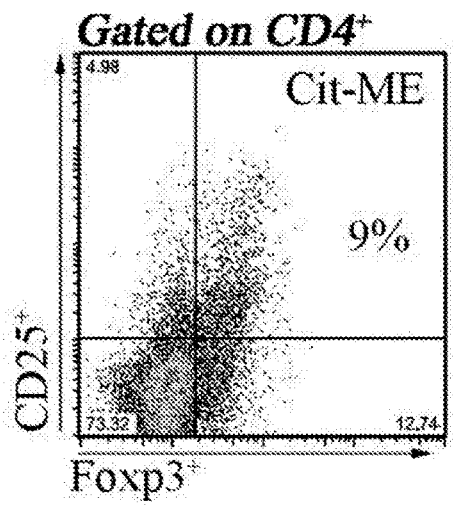
FIG. 12 presents FACS two dimensional dot plots of regulatory T cells treated with Cit-ME (A), Non-Cit-ME (B) and no treatment (C) stained with anti-CD4-FITC, anti-CD25-APC, gated for anti-Foxp3-PE and the corresponding analyses (D; n=8 for each treatment).
Figure 12B:
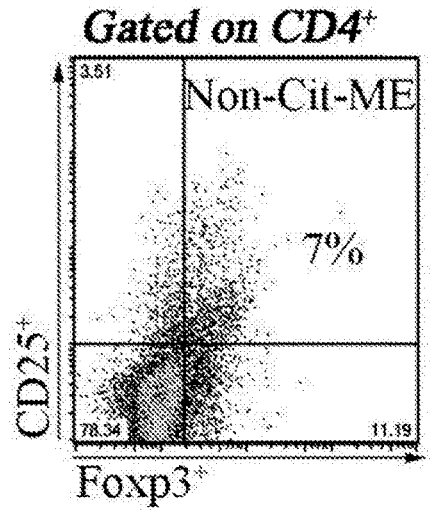
Figure 12C:
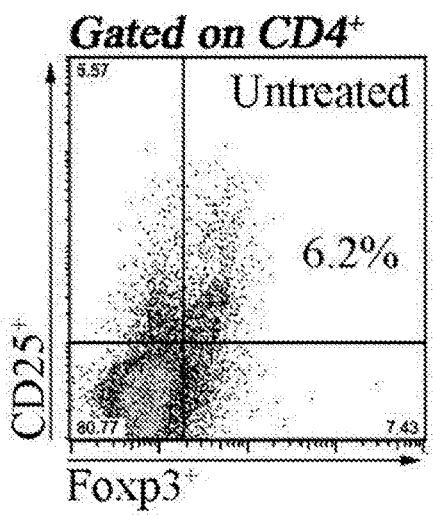
Figure 12D:
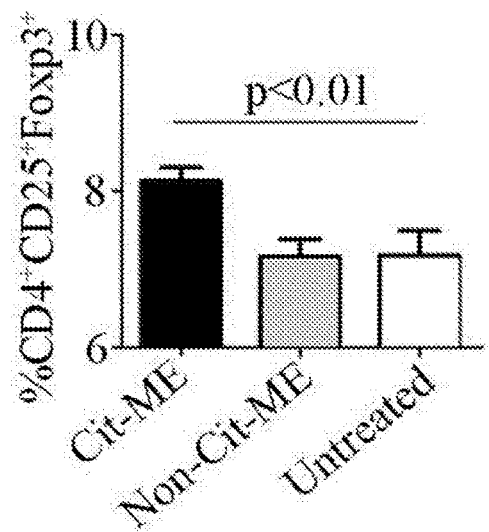

Splenocytes from rats at day 28 post disease induction were stained with anti-CD4-FITC, anti-CD25-APC, and anti-Foxp3-PE (eBioscience) mAbs and analyzed by FACS. In representative outputs as shown in FIG. 12A-C, Regulatory T cells subpopulation was higher in Cit-ME treated rats (9%), compared to 7% and 6.2% in Non-Cit-ME peptide and untreated rats, respectively. Statistical analysis of the results is shown in FIG. 12D (Cit-ME n=9, Non-Cit-ME n=11, untreated rats n=7). A significant increase in percentage of $CD4^+CD25^+FoxP3^+$ regulatory T cells subset was observed in the spleens of Cit-ME treated rats (8.13±0.17) compared to Non-Cit-ME peptide and untreated rats (6.97±0.22, 7.17±0.31, respectively, p<0.01).

Example 12: Effect of Treating AIA Mice with Cit-ME on IL-17+ Population

Distribution of pathogenic $CD4^+IL-17^+$ T cells in the spleen of experimental rats was assessed by FACS. Representative results of Cit-ME treated and non-treated cells (FIG. 13A-13B, respectively) show that IL-17+ population reduced from 2% to 0.6% following treatment with Cit-ME peptides compared to untreated rats. Statistical analysis of FACS results (n=8) shows that the population of $CD4^+IL-17^+$-expressing splenocytes was significantly lower (p<0.03) in Cit-ME treated AIA rats (0.68±0.1) compared to untreated AIA rat (1.14±0.2) (FIG. 13C).

To validate the effect of the peptides on $CD4^+IL-17^+$ populations as determined by FACS, the expression of IL-17 in the spleen was evaluated using RT-PCR. cDNA was extracted from the spleens of 8 rats per treatment (including control), and gene expression of IL-17 was assessed using the following RT-PCR primers: forward 5'-TGGCGGT-TCTCCTTCAGTC-3' (SEQ ID NO: 17) and reverse 5'-CG-GTGTAGTCATCTTCATCTCC-3' (SEQ ID NO: 18). A significant reduction in the mean relative expression level of IL-17 mRNA was observed in Cit-ME compared to control (FIG. 13D). Thus, the RT-PCR data was in line with the FACS analyses.

Example 13: The Effect of Cit-ME and Non-Cit-ME on T Cell Apoptosis

Figure 14A:
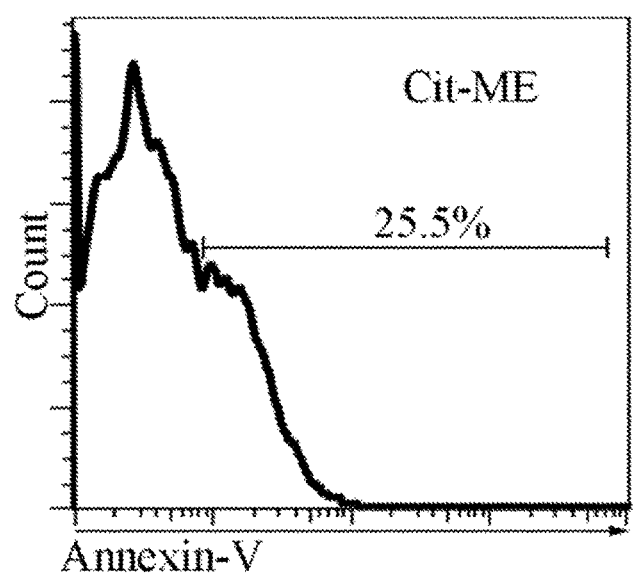
FIGS. 14A-14E are representative histograms of T cells derived from the spleen of AIA rats treated with Cit-Me (A), non-Cit-ME (B) or control (untreated; C), an overlay histogram of Cit-ME and control (D) and the corresponding statistical analysis (n=2; E).
Figure 14B:
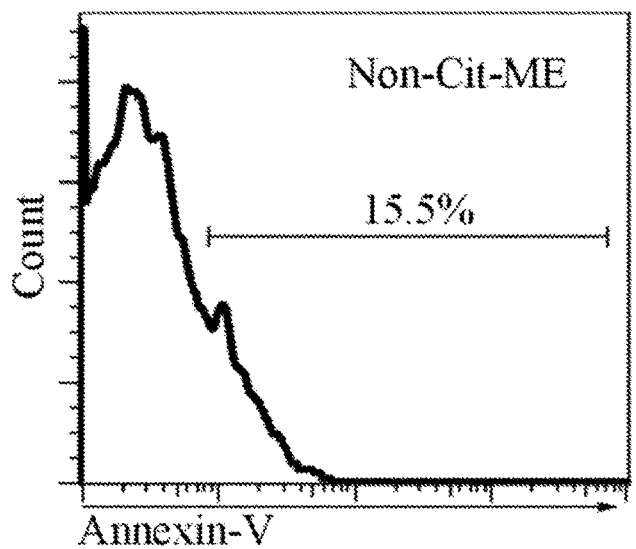
Figure 14C:
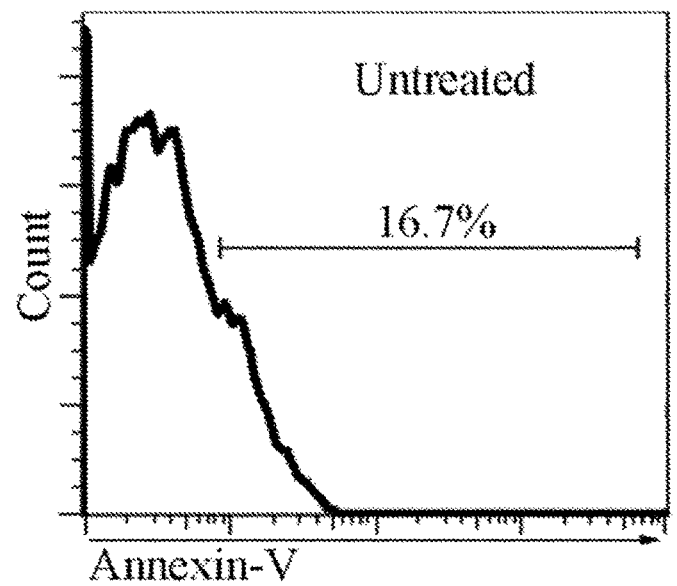
Figure 14D:
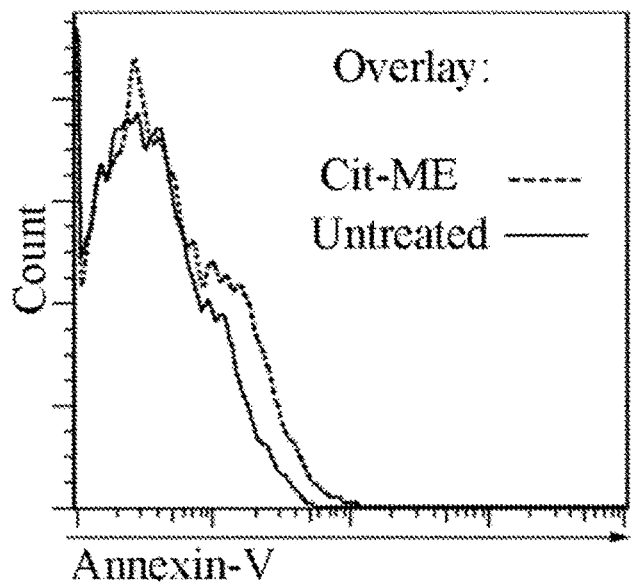
Figure 14E:
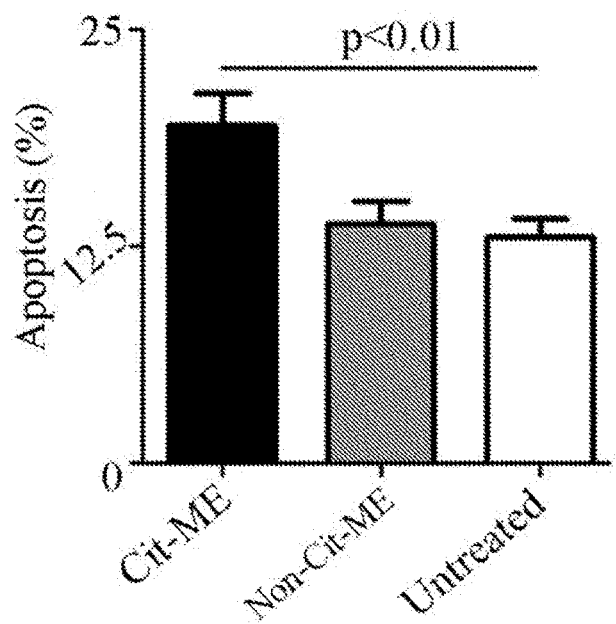

To assess apoptosis of T cells derived from the spleen of treated rats, the Annexin V/PI staining method was preformed. FIGS. 14A-14C are representative histograms of cells treated with Cit-Me (FIG. 14A), non-Cit-Me (FIG. 14B) or untreated (FIG. 14C). The histograms present apoptosis measured by Annexin V⁺. First, cells were gated for PI and CD4⁺ and next analyzed for percentage of Annexin-V positive cells. FIG. 14D shows overlay histogram of Annexin-V positive staining of splenocytes derived from Cit-ME and untreated rats. FIG. 14E shows the mean values obtained from two independent experiments. A significant increase (p<0.01) in the mean apoptotic rate was determined in cells from the spleen of Cit-ME treated rats (19.5±1.8%) in comparison with Non-Cit-ME or control (13.8±1.3% and 13±1%, respectively).

Figure 14F:
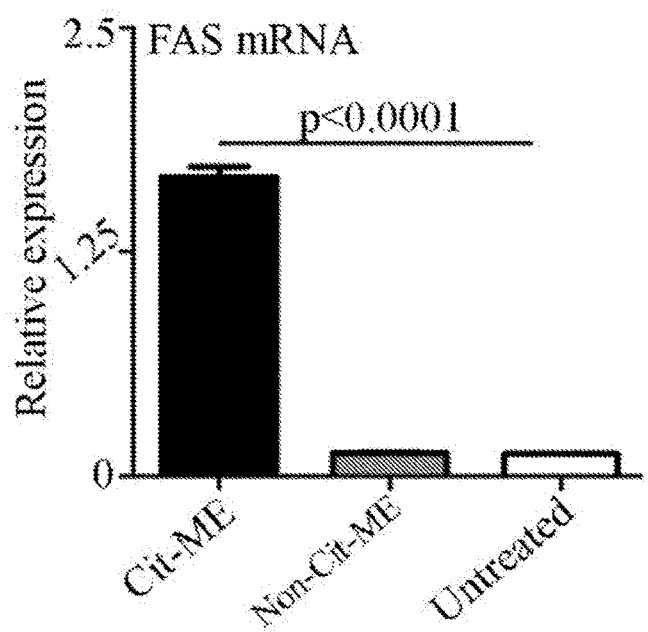
FIG. 14F presents the relative expression of mRNA FAS receptor in the splenocytes of AIA rats treated with Cit-ME, Non-Cit-ME or untreated AIA rats.

To examine whether Cit-ME affects apoptosis through the FAS receptor pathway, FAS mRNA expression in splenocytes was evaluated (FIG. 14F), using the following RT-PCR primers: forward 5'-TGGCTGTCCTGCCTCTGGT-3' (SEQ ID NO: 19) and reverse 5'-CGAACGCTCCTCT-TCAACTCC-3' (SEQ ID NO: 20). As shown in FIG. 14F, the mean relative expression level of FAS mRNA was significantly higher (p<0.0001) in Cit-ME treated rats compared to Non-Cit-ME and control groups.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A synthetic peptide comprising the amino acid sequence set forth in SEQ ID NO: 1.

2. A method of treating an autoimmune disease comprising administering to a subject in need thereof a therapeutically effective amount of a pharmaceutical composition comprising a synthetic peptide and a pharmaceutically acceptable carrier, wherein said peptide comprises the amino acid sequence set forth in SEQ ID NO: 1, wherein the autoimmune disease is rheumatoid arthritis.

3. A pharmaceutical composition comprising the synthetic peptide of claim 1 and a carrier.

4. The pharmaceutical composition of claim 3 for subcutaneous administration.

5. The method of claim 2, wherein said subject is selected from the group consisting of: a patient afflicted with said disease or disorder, a patient afflicted with said disease or disorder wherein said patient is in remission, a patient afflicted with said disease or disorder having manifested symptoms associated with said disease or disorder, and any combination thereof.

6. The method of claim 2, wherein said subject is an ACPA$^+$ RA patient.

7. The method of claim 2, wherein said treating includes down regulation of TNF-$\alpha$ expression.

8. The method of claim 2, wherein said treating includes down regulation of IFN-$\gamma$ expression.

9. The method of claim 2, wherein said treating includes up regulation of the expression of TGF-$\beta$.

10. The method of claim 2, wherein said treating includes expansion of T regulatory cell population.

11. The method of claim 2, wherein said treating includes down-regulation of pathogenic Th17 cells.

12. The method of claim 2, wherein said treating includes reducing the population of CD4$^+$IL-17$^+$-expressing splenocytes.

13. The method of claim 2, wherein said treating includes increasing the apoptotic rate of T cells derived from splenocytes.

\* \* \* \* \*

```
                         SEQUENCE LISTING

<160> NUMBER OF SEQ ID NOS: 22

<210> SEQ ID NO 1
    <211> LENGTH: 25
    <212> TYPE: PRT
    <213> ORGANISM: Artificial
    <220> FEATURE:
    <223> OTHER INFORMATION: Synthetic peptide
    <220> FEATURE:
    <221> NAME/KEY: peptide
    <222> LOCATION: (1)..(25)
    <223> OTHER INFORMATION: X=citrulline residues
    <220> FEATURE:
    <221> NAME/KEY: peptide
    <222> LOCATION: (1)..(25)
    <223> OTHER INFORMATION: X=Citrulline residue

<400> SEQUENCE: 1

Val Xaa Leu Xaa Ser Ser Val Glu Ser Thr Xaa Gly Arg Ser Xaa Pro
    1               5                   10                  15

Ala Pro Pro Pro Ala Xaa Gly Leu Thr
                20                  25

<210> SEQ ID NO 2
    <211> LENGTH: 15
    <212> TYPE: PRT
    <213> ORGANISM: Artificial
    <220> FEATURE:
    <223> OTHER INFORMATION: Synthetic peptide
    <220> FEATURE:
    <221> NAME/KEY: peptide
    <222> LOCATION: (1)..(15)
    <223> OTHER INFORMATION: X=Citrulline residue

<400> SEQUENCE: 2

Xaa Pro Ala Pro Pro Pro Ile Ser Gly Gly Gly Tyr Xaa Ala Xaa
    1               5                   10                  15

<210> SEQ ID NO 3
    <211> LENGTH: 21
    <212> TYPE: PRT
    <213> ORGANISM: Artificial
    <220> FEATURE:
    <223> OTHER INFORMATION: Synthetic peptide
    <220> FEATURE:
    <221> NAME/KEY: peptide
    <222> LOCATION: (1)..(21)
    <223> OTHER INFORMATION: X=Citrulline residue

<400> SEQUENCE: 3
```

His Gln Cys His Gln Glu Ser Thr Xaa Gly Arg Ser Arg Gly Arg Cys
1               5                   10                  15

Gly Arg Ser Gly Ser
            20

<210> SEQ ID NO 4
<211> LENGTH: 25
<212> TYPE: PRT
<213> ORGANISM: Artificial
<220> FEATURE:
<223> OTHER INFORMATION: Synthetic peptide

<400> SEQUENCE: 4

Val Arg Leu Arg Ser Ser Val Glu Ser Thr Arg Gly Arg Ser Arg Pro
1               5                   10                  15

Ala Pro Pro Pro Ala Arg Gly Leu Thr
            20                  25

<210> SEQ ID NO 5
<211> LENGTH: 7
<212> TYPE: PRT
<213> ORGANISM: Artificial
<220> FEATURE:
<223> OTHER INFORMATION: Synthetic peptide

<400> SEQUENCE: 5

Val Arg Leu Arg Ser Ser Val
1               5

<210> SEQ ID NO 6
<211> LENGTH: 7
<212> TYPE: PRT
<213> ORGANISM: Artificial
<220> FEATURE:
<223> OTHER INFORMATION: Synthetic peptide

<400> SEQUENCE: 6

Glu Ser Thr Arg Gly Arg Ser
1               5

<210> SEQ ID NO 7
<211> LENGTH: 6
<212> TYPE: PRT
<213> ORGANISM: Artificial
<220> FEATURE:
<223> OTHER INFORMATION: Synthetic peptide

<400> SEQUENCE: 7

Arg Pro Ala Pro Pro Pro
1               5

<210> SEQ ID NO 8
<211> LENGTH: 5
<212> TYPE: PRT
<213> ORGANISM: Artificial
<220> FEATURE:
<223> OTHER INFORMATION: Synthetic peptide

<400> SEQUENCE: 8

Ala Arg Gly Leu Thr
1               5

<210> SEQ ID NO 9
<211> LENGTH: 7
<212> TYPE: PRT

```
<213> ORGANISM: Artificial
<220> FEATURE:
<223> OTHER INFORMATION: Synthetic peptide
<220> FEATURE:
<221> NAME/KEY: Peptide
<222> LOCATION: (1)..(7)
<223> OTHER INFORMATION: X=Citrulline residue

<400> SEQUENCE: 9

Val Xaa Leu Arg Ser Ser Val
1               5

<210> SEQ ID NO 10
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: peptide
<222> LOCATION: (1)..(7)
<223> OTHER INFORMATION: X=Citrulline residue

<400> SEQUENCE: 10

Val Arg Leu Xaa Ser Ser Val
1               5

<210> SEQ ID NO 11
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: peptide
<222> LOCATION: (1)..(7)
<223> OTHER INFORMATION: X=Citrulline residue

<400> SEQUENCE: 11

Val Xaa Leu Xaa Ser Ser Val
1               5

<210> SEQ ID NO 12
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: peptide
<222> LOCATION: (1)..(7)
<223> OTHER INFORMATION: X=Citrulline residue

<400> SEQUENCE: 12

Glu Ser Thr Xaa Gly Arg Ser
1               5

<210> SEQ ID NO 13
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: Peptide
<222> LOCATION: (1)..(7)
<223> OTHER INFORMATION: X=Citrulline residue

<400> SEQUENCE: 13

Glu Ser Thr Arg Gly Xaa Ser
```

```
<210> SEQ ID NO 14
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: Peptide
<222> LOCATION: (1)..(7)
<223> OTHER INFORMATION: X=Citrulline residue

<400> SEQUENCE: 14

Glu Ser Thr Xaa Gly Xaa Ser
1               5

<210> SEQ ID NO 15
<211> LENGTH: 6
<212> TYPE: PRT
<213> ORGANISM: Artificial
<220> FEATURE:
<223> OTHER INFORMATION: Synthetic peptide
<220> FEATURE:
<221> NAME/KEY: Peptide
<222> LOCATION: (1)..(5)
<223> OTHER INFORMATION: X=Citrulline residue

<400> SEQUENCE: 15

Xaa Pro Ala Pro Pro Pro
1               5

<210> SEQ ID NO 16
<211> LENGTH: 5
<212> TYPE: PRT
<213> ORGANISM: Artificial
<220> FEATURE:
<223> OTHER INFORMATION: Synthetic residue
<220> FEATURE:
<221> NAME/KEY: Peptide
<222> LOCATION: (1)..(5)
<223> OTHER INFORMATION: X=Citrulline residue

<400> SEQUENCE: 16

Ala Xaa Gly Leu Thr
1               5

<210> SEQ ID NO 17
<211> LENGTH: 19
<212> TYPE: DNA
<213> ORGANISM: Artificial
<220> FEATURE:
<223> OTHER INFORMATION: Symthetic oligo

<400> SEQUENCE: 17
tggcggttct ccttcagtc                                               19

<210> SEQ ID NO 18
<211> LENGTH: 22
<212> TYPE: DNA
<213> ORGANISM: Artificial
<220> FEATURE:
<223> OTHER INFORMATION: Synthetic oligo

<400> SEQUENCE: 18
cggtgtagtc atcttcatct cc                                           22

<210> SEQ ID NO 19
```

```
<211> LENGTH: 19
<212> TYPE: DNA
<213> ORGANISM: Artificial
<220> FEATURE:
<223> OTHER INFORMATION: Synthetic oligo

<400> SEQUENCE: 19
tggctgtcct gcctctggt                                                  19

<210> SEQ ID NO 20
<211> LENGTH: 21
<212> TYPE: DNA
<213> ORGANISM: Artificial
<220> FEATURE:
<223> OTHER INFORMATION: Synthetic oligo

<400> SEQUENCE: 20
cgaacgctcc tcttcaactc c                                               21

<210> SEQ ID NO 21
<211> LENGTH: 12
<212> TYPE: PRT
<213> ORGANISM: artificial
<220> FEATURE:
<223> OTHER INFORMATION: synthetic peptide
<220> FEATURE:
<221> NAME/KEY: Peptide
<222> LOCATION: (1)..(12)
<223> OTHER INFORMATION: X=Citrulline residue

<400> SEQUENCE: 21

Ala Xaa Gly Leu Thr Gly Xaa Pro Gly Asp Ala Lys
1               5                   10

<210> SEQ ID NO 22
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: Peptide
<222> LOCATION: (1)..(14)
<223> OTHER INFORMATION: X-Citrullinated residue

<400> SEQUENCE: 22

Ser Ala Val Arg Ala Xaa Ser Ser Val Pro Gly Val Arg Lys
1               5                   10
```